(12) United States Patent
Yin

(10) Patent No.: US 7,294,479 B2
(45) Date of Patent: Nov. 13, 2007

(54) COMPOSITIONS, KIT AND ONE-STEP METHOD FOR MONITORING COMPOUNDS HAVING ANTI-FACTOR $X_A$ AND/OR ANTI FACTOR $II_A$ ACTIVITIES

(76) Inventor: Thye Yin, 7450 Whitehall Colonial La., St. Louis, MO (US) 63119

( * ) Notice: Subject to any disclaimer, the term of this patent is extended or adjusted under 35 U.S.C. 154(b) by 0 days.

(21) Appl. No.: 11/127,540

(22) Filed: May 11, 2005

(65) Prior Publication Data

US 2005/0255535 A1     Nov. 17, 2005

Related U.S. Application Data

(60) Provisional application No. 60/570,312, filed on May 11, 2004.

(51) Int. Cl.
*C12Q 1/56* (2006.01)
*G01N 33/86* (2006.01)

(52) U.S. Cl. .......................... 435/13; 436/69
(58) Field of Classification Search .............. None
See application file for complete search history.

(56) References Cited

U.S. PATENT DOCUMENTS

| | | | |
|---|---|---|---|
| 4,234,682 A | 11/1980 | Bartl et al. | |
| 4,851,336 A | 7/1989 | Yin | |
| 4,946,775 A * | 8/1990 | Yin ............................. | 435/13 |
| 5,110,727 A | 5/1992 | Oberhardt | |
| 5,192,689 A | 3/1993 | Hemker et al. | |
| 5,308,755 A | 5/1994 | Nesheim et al. | |
| 5,409,959 A | 4/1995 | Hwang et al. | |
| 5,547,850 A | 8/1996 | Nowak et al. | |
| 5,547,944 A | 8/1996 | Mascellani et al. | |
| 5,576,304 A | 11/1996 | Kakkar et al. | |
| 5,702,912 A | 12/1997 | Hemker et al. | |
| 6,114,135 A | 9/2000 | Goldstein | |
| 6,140,062 A | 10/2000 | Wagenvoord | |
| 6,150,114 A | 11/2000 | Feigen et al. | |
| 6,156,734 A * | 12/2000 | Grinnell et al. ................ | 514/21 |
| 6,194,394 B1 | 2/2001 | Hawkins | |
| 6,528,273 B2 | 3/2003 | Hawkins | |
| 6,566,140 B2 * | 5/2003 | Mann et al. ................... | 436/69 |
| 6,630,989 B1 | 10/2003 | Caputo et al. | |
| 6,645,768 B1 | 11/2003 | Tejidor et al. | |
| 6,699,718 B1 | 3/2004 | Bruegger | |
| 2003/0104508 A1 | 6/2003 | Gempeter | |

FOREIGN PATENT DOCUMENTS

WO      WO 01/44493 A2    6/2001

OTHER PUBLICATIONS

Nesheim et al., "Isolation and Characterization of Single Chain Bovine Factor V", JBC (1979), 254 (2), 508-17.*
Barton et al., "Reactions of activated factor X-phosphatide mixtures in vitro and in vivo," *J. Lipid Res.* 11:87-95 (1970).
Bell et al., *Nature*, 174:880 (1954).
Biggs et al, *Human Blood Coagulation and Its Disorders*, 3rd edition (1962), pp. 54-66.
Biggs, *Human Blood Coagulation, Haemostasis and Thrombosis*, (1972), pp. 592-601.
Campbell, PJ et al., "HEPTEST: a suitable method for monitoring heparin during pregnancy," *Clin Lab Haematol*, Jun. 21:193-9 (1999).
Dahlback, "Human coagulation factor V purification and thrombin-catalyzed activation" *J. Clin. Invest.*, 66:583-91 (1980).
Harenberg, J. et al., "Comparative study on a new one-stage clotting assay for heparin and its low molecular weight derivatives," *Haemostasis*, 19:13-20 (1989).
International Search Report dated May 19, 2006 issued on International Application No. PCT/US2005/16249.
Kane et al., "Purification and characterization of human coagulation factor V," *J. Biol. Chem.*, 256:1002-1007 (1980).
Kristensen, HI et al., "Effect of tissue factor pathway inhibitor (TFPI) in the HEPTEST assay and in an amidolytic anti factor Xa assay for LMW heparin," *Thromb Haemost*, Sep. 7;68(3):310-4 (1992).
Martinez et al., Deciphering the plasma membrane hallmarks of apoptotic cells: Phosphatidylserine transverse redistribution and calcium entry, *BMC Cell Biology*, 2:20 (2001).
Papahodjoupolus et al., *Proc. Soc. Exp. Biol. Med.*, 111:412 (1962).
Smirnov et al., "A chimeric protein C containing the prothrombin Gla domain exhibits increased anticoagulant activity and altered phospholipid specificity," *J Biol Chem.*, 273:9031-9040 (1998).
Welsby, IJ. et al., "Activated clotting time systems vary in precision and bias and are not interchangeable when following heparin management protocols during cardiopulmonary bypass," *J Clin Monit Comput.*, Jul. 17(5):287-92 (2002).
Yin et al, "Bovine thrombin and activated factor X. Separation and purification," *J. Biol. Chem*, 243:112-117 (1968).
Yin et al, "Plasma heparin: a unique, practical, submicrogram-sensitive assay," *J. Lab. Clin. Med.*, 81:298 (1973).
Zwaal, RF. Et al., "Lipid-protein interactions in blood coagulation," *Biochim Biophys Acta.*, Nov. 10;1376(3):433-53 (1998).
Hendrice, C. et al., "Effects of aprotinin on blood loss, heparin monitoring tests, and heparin doses in patients undergoing coronary artery bypass", *Journal of Cardiothoracic & Vascular Anesthesia*, 9(3):245-9, 1995. (Abstract only).

(Continued)

*Primary Examiner*—Sandra E. Saucier
(74) *Attorney, Agent, or Firm*—Knobbe Martens Olson & Bear LLP

(57) ABSTRACT

Provided are compositions and methods for accurate determination of the concentration of anticoagulant in a sample such as a blood or plasma sample. The compositions can contain a Factor X compound and Factor V compound, and additional components as well. Methods for performing the assay include one-step methods in which a sample is added to a coagulation assay composition, and time is monitored from the point of adding the sample and coagulation assay composition to an endpoint, such as clot formation.

20 Claims, 4 Drawing Sheets

OTHER PUBLICATIONS

Hellstern, Peter et al., "Heparin Monitoring during Cardiopulmonary bypass Surgery using the One-Step Point-of-Care Whole Blood Anti-Factor-Xa Clotting Assay Heptest-POC-HI™", *Journal of Extracorporeal Circulation Technology* 2007 (publication pending).

Hansen, Roland et al., "A quick Anti-Xa-Activity-Based Whole Blood Coagulation Assay for Monitoring Unfractionated Heparin During Cardiopulmonary Bypass: A Pilot Investigation", *Anesth Analg.*, 91:533-8, 2000.

Kristensen et al., "A Fast Amidolytic Anti-Factore Xa Assay Not Influenced by Aprotinin for Monitoring of Heparin During Cardio-Pulmonary By-Pass Operation", Abstracts of XIVth Congress of the International Society on Thrombosis and Haemostasis, New York, New York, USA, Jul. 4-9, 1993, published in *Thrombosis and Haemostasis—Journal of the International Society on Thrombosis and Haemostasis*, 69(6):538-1455, Jun. 30, 1993. ISSN: 0340-6245. Abstract only.

* cited by examiner

Flow chart for the preparation of Heptest-POC-Hi Reagents

Flow chart for the preparation of HHDR

COMPOSITIONS, KIT AND ONE-STEP METHOD FOR MONITORING COMPOUNDS HAVING ANTI-FACTOR $X_A$ AND/OR ANTI FACTOR $II_A$ ACTIVITIES

This application claims priority under 35 U.S.C. §119(e) to U.S. Provisional Application Ser. No. 60/570,312, filed on May 11, 2004, to Thye Yin. The subject matter of the above-noted patent application is herein incorporated in its entirety.

BACKGROUND

1. Technical Field

The claimed subject matter relates to testing blood clotting in blood, and more particularly to determining the anti-Factor $X_a$ and/or anti Factor $II_a$ activities of compounds in a blood sample.

2. Background

The determination of heparin establishes an important parameter for the supervision of heparin treatment, which is often administered in the presence of a threat of thrombosis. Heparin forms with antithrombin III (AT III) a complex that inhibits the proteolytic activity of $FX_a$ and thrombin. Heparin treatment is often applied in the presence of a threat of thrombosis (e.g. before surgical interventions). Adjustment of heparin concentration is therefore important. If the dose is too low, there is the danger of thrombosis or embolism, which can result in death. Excessively high heparin concentrations, however, result in bleeding. The quantitative analysis of heparin, therefore, is one of the tests most frequently performed in a blood testing laboratory.

In 1973 Yin and co-workers developed the first quantitative assay method for the in vitro measurement of heparin in plasma based on Factor $X_a$ neutralization (J. Lab. Clin. Med. 81:298, 1973). This assay method could detect less than 0.02 units of heparin per milliliter of plasma. However, the assay is cumbersome and time consuming to perform. It is a two-stage assay, and requires much manual manipulation. In the first-stage of the assay, the patient's plasma sample is incubated with the sample plasma, buffer, and a known excess of Factor $X_a$ for a predetermined time period, after which a sub sample from this primary reaction mixture is removed and assayed for residual Factor $X_a$ activity. The latter step constitutes the second-stage of the assay. The residual Factor $X_a$ activity is measured by the addition of the test sample to another test tube, and to it calcium chloride, cephalin in bovine plasma are added separately in timed fashion. Other assays that presently exist are either cumbersome or limited in scope of application. Therefore, a need exists for improved heparin assay methods.

SUMMARY

The details of one or more embodiments of the invention are set forth in the description below. Other features, objects, and advantages of the invention will be apparent from the description and drawings, and from the claims.

Provided herein are blood coagulation assay compositions that contain a Factor X compound and a Factor V compound. The compositions can also include a variety of additional components such as a multivalent cation, lipid or detergent, fibrinogen, anticoagulant, prothrombin complex, normal plasma. In one embodiment, the Factor V compound is a component of a plasma fraction. The compositions can be present in a vessel substantially free of liquid or gaseous $H_2O$. The compositions can be present in a vessel in substantially unreacted or unactivated form.

Also provided herein are methods for preparing a blood coagulation assay composition by placing Factor X compound into a vessel and placing Factor V compound into the vessel in such a manner that the components do not substantially react. In one embodiment, the components are added in such a manner that any liquid placed into the vessel is flash frozen upon placement into the vessel.

Also provided herein are methods of assaying coagulation of a sample by mixing a sample with a coagulation assay composition and determining the time period beginning upon mixing the sample and coagulation assay composition and ending upon clot formation. In one embodiment, only a single mixing step is required.

Provided herein are blood coagulation assay compositions that contain a Factor X compound and Factor V compound. The compositions provided herein can be substantially free of liquid or gaseous $H_2O$. The compositions provided herein can contain components of the composition that are substantially unreacted with one another. The compositions provided herein can be substantially free of products of a clotting reaction. In the compositions provided herein, Factor X compound can be substantially free of antithrombin III bound thereto. In the compositions provided herein, addition of blood or a blood sample to the composition can initiate a clotting reaction. In the compositions provided herein, substantially all of the phospholipid of the composition can be aqueously dispersed. In the compositions provided herein, substantially all of the calcium salt of the composition can be aqueously soluble. In the compositions provided herein, substantially all of the Factor Xa of the composition can be aqueously soluble. In the compositions provided herein, substantially all of the Factor Xa of the composition can be unbound by antithrombin III. The compositions provided herein can be further characterized by providing a linear anticoagulant curve when anticoagulant concentration is plotted versus clotting time. In the compositions provided herein, substantially all of the Factor V compound of the composition can be aqueously soluble. In the compositions provided herein, substantially all components of the composition can be aqueously soluble. In the compositions provided herein, the composition can be substantially free of Factor IIa. In the compositions provided herein, the composition can be substantially free of fibrin.

The compositions provided herein can further contain a multivalent cation. In the compositions provided herein, the multivalent cation can be selected from the group consisting of $Mg^{2+}$ ion and $Ca^{2+}$ ion. In the compositions provided herein, the multivalent cation can be $Ca^{2+}$.

The compositions provided herein can further contain lipid or detergent. In the compositions provided herein, the lipid or detergent can include two or more different lipids or detergent. In the compositions provided herein, the lipid can be from a biological source. In the compositions provided herein, the lipid can be rabbit brain cephalin.

The compositions provided herein can include a plasma fraction. In the compositions provided herein, Factor V compound can be a component of a plasma fraction. In the compositions provided herein, the plasma fraction can be characterized by a property selected from the group consisting of: (i) it does not clot by itself for at least 24 hours at 37° C.; (ii) it forms a firm clot in the presence of added thrombin; (iii) it contains at least 25% of Factor V compound that is present per unit volume in normal human plasma; (iv) it provides a linear anticoagulant curve using a standard anticoagulant preparation; and (v) any combination of (i), (ii), (iii) or (iv). The compositions provided herein can further comprise a plasma fraction substantially free of Factors II, VII, IX, and X.

The compositions provided herein can contain additional components, such as components of a blood clotting reaction. The compositions provided herein can further comprise fibrinogen. The compositions provided herein can further comprise a plasma fraction containing fibrinogen. The compositions provided herein can further comprise a plasma fraction containing Factor V compound, and further can contain fibrinogen and lipid or detergent added thereto. The compositions provided herein can further contain prothrombin complex. The compositions provided herein can further contain a plasma fraction containing prothrombin complex. The compositions provided herein can further contain an anticoagulant. The compositions provided herein can further contain a plasma fraction containing anticoagulant. The compositions provided herein can further contain normal plasma. The compositions provided herein can further contain a plasma fraction with normal plasma added thereto. The compositions provided herein can further contain antithrombin III. The compositions provided herein can further contain a plasma fraction containing antithrombin III. The compositions provided herein can further contain a plasma fraction containing Factor V compound, and can further contain prothrombin complex, anticoagulant, lipid or detergent, and normal plasma added thereto. The compositions provided herein can further contain a procoagulant phospholipid. The compositions provided herein can further contain a brain phospholipid. The compositions provided herein can further contain an anionic phospholipid. The compositions provided herein can further contain a cationic detergent. The compositions provided herein can further contain a phospholipid selected from the group consisting of phosphatidylethanolamine, phosphatidylserine, phosphatidylinositol, phosphatidylcholine, and cardiolipin. The compositions provided herein can further contain a plurality of phospholipids. In the compositions provided herein, the plurality of phospholipids can contain two or more phospholipids selected from the group consisting of phosphatidylethanolamine, phosphatidylserine, phosphatidylinositol, phosphatidylcholine, and cardiolipin. The compositions provided herein can further contain a calcium salt. In the compositions provided herein, the calcium salt can be a calcium halide. In the compositions provided herein, the calcium salt can be calcium chloride. The compositions provided herein can be substantially free of any gaseous, liquid or solid $H_2O$. The compositions provided herein can contain solid $H_2O$. The compositions provided herein can be a lyophilized composition. The compositions provided herein can further contain a dessicant. In the compositions provided herein, the Factor X compound can be Factor $X_a$. In the compositions provided herein, the Factor V compound can be Factor V. The compositions provided herein can further contain benzamidine. The compositions provided herein can provide a linear correlation between clotting time and heparin concentration range, wherein the heparin concentration range is selected from the group consisting of 0 units/mL to about 20 units/mL, 0 units/mL to about 15 units/mL, 0 units/mL to about 12 units/mL, 0 units/mL to about 10 units/mL, 0 units/mL to about 7.5 units/mL, and 0 units/mL to about 5 units/mL. The compositions provided herein can provide a linear correlation between clotting time and hirudin concentration range, wherein the hirudin concentration range is selected from the group consisting of 0 µg/mL to about 20 µg/mL, 0 µg/mL to about 15 µg/mL, 0 µg/mL to about 12 µg/mL, 0 µg/mL to about 10 µg/mL, 0 µg/mL to about 7.5 µg/mL, and 0 µg/mL to about 5 µg/mL. The compositions provided herein can provide a linear correlation between clotting time and heparin concentration range, wherein the heparin concentration range is selected from the group consisting of 0 units/mL to 20 units/mL, 0 units/mL to 15 units/mL, 0 units/mL to 12 units/mL, 0 units/mL to 10 units/mL, 0 units/mL to 7.5 units/mL, and 0 units/mL to 5 units/mL. The compositions provided herein can provide a linear correlation between clotting time and hirudin concentration range, wherein the hirudin concentration range is selected from the group consisting of 0 µg/mL to 20 µg/mL, 0 µg/mL to 15 µg/mL, 0 µg/mL to 12 µg/mL, 0 µg/mL to 10 µg/mL, 0 µg/mL to 7.5 µg/mL, and 0 µg/mL to 5 µg/mL.

The coagulation assay compositions provided herein also can be characterized such that Factor X compound and Factor V compound are substantially not admixed. In another embodiment, the coagulation assay compositions are characterized such that Factor X compound is present in a discrete solid form and Factor V compound is present in a discrete solid form, and wherein the discrete solid form of Factor X compound contacts substantially only the surface of the discrete solid form of Factor V compound. In another embodiment, the coagulation assay compositions are characterized such that Factor X compound is present in a discrete solid form and Factor V compound is present in a discrete solid form, and wherein the discrete solid form of Factor X compound contacts no more than substantially only the surface of the discrete solid form of Factor V compound. In another embodiment, the coagulation assay compositions are characterized such that Factor X compound and Factor V compound are present in discrete separate portions, wherein the discrete separate portions contact substantially only the surface of one another. In another embodiment, the coagulation assay compositions are characterized such that Factor X compound and Factor V compound are present in discrete separate portions, wherein the discrete separate portions contact nor more than substantially only the surface of one another. In another embodiment, the coagulation assay compositions are characterized such that Factor X compound is admixed with at least one admixing compound, wherein the admixing compound is substantially not admixed with Factor V compound. In another embodiment, the coagulation assay compositions are characterized such that Factor X compound is admixed with at least one admixing compound, wherein the admixing compound is substantially unreacted with Factor V compound. In another embodiment, the coagulation assay compositions are characterized such that Factor V compound is admixed with at least one admixing compound, wherein the admixing compound is substantially not admixed with Factor X compound. In another embodiment, the coagulation assay compositions are characterized such that Factor V compound is admixed with at least one admixing compound, wherein the admixing compound is substantially unreacted with Factor X compound. In another embodiment, the coagulation assay compositions are characterized such that Factor X compound is not in fluid mixture with Factor V compound. In another embodiment, the coagulation assay compositions are characterized such that Factor X compound is not in a fluid composition containing Factor V compound. In another embodiment, the coagulation assay compositions are characterized such that wherein addition of an aqueous liquid to the composition causes Factor X compound and Factor V compound to become substantially admixed. In another embodiment, the coagulation assay compositions are characterized such that Factor X compound is present in excess relative to the amount of sample to be added to the composition. In another embodiment, the coagulation assay compositions are characterized such that Factor V compound is present in excess relative to the amount of sample to be added to the composition. In another embodiment, the coagulation assay compositions are characterized such that multivalent cation salt is present in excess relative to the amount of sample to be added to the composition.

Also provided herein are combinations, including any of the compositions provided herein contained in a vessel. In the combinations provided herein, the vessel can be sealed under vacuum. In the combinations provided herein, the vessel can be sealed with a vapor-impermeable seal. In the combinations provided herein, the vessel can be a glass vessel. In the combinations provided herein, the glass vessel can be siliconized. In the combinations provided herein, the glass vessel can be homogenously siliconized. The combinations provided herein can further contain a magnetically influenceable particle within the vessel. In the combinations provided herein, the magnetically influenceable particle can be a steel particle. In the combinations provided herein, the steel particle can be a steel ball. In the combinations provided herein, the steel ball can contain a diameter ranging from about 1 mm to about 3 mm, or 1 mm to 3 mm. In the combinations provided herein, the steel ball can contain a diameter of about 2 mm or 2 mm. In the combinations provided herein, the steel ball can contain a diameter of about 2.4 mm or 2.4 mm.

Also provided herein are kits, where the kit can contain any of the combinations provided herein, and one additional element. The kits provided herein can further contain instructions for use. In the kits provided herein, the instructions for use can include a reference for quantitating the results of a coagulation assay. For example, a kit can contain a data sheet for interpreting the results of the coagulation assay, such as a data sheet that provides heparin and/or hirudin concentration for particular clotting times. In the kits provided herein, the instructions for use can include a calibration curve. The kits provided herein can further contain a blood collection device. In the kits provided herein, the blood collection device can be a vessel. In the kits provided herein, the blood collection device can contain a coagulation suppressing solution. In the kits provided herein, the blood collection device contains sodium citrate. The kits provided herein can further contain an anticoagulant. In the kits provided herein, the anticoagulant can be selected from the group consisting of heparin and hirudin. The kits provided herein can further contain a vessel mixer. In the kits provided herein, the vessel mixer can be a vortex mixer. The kits provided herein can further contain a magnetic device for moving a magnetic particle located in the vessel. In the kits provided herein, the magnetic device can be a magnetic plate. In the kits provided herein, the magnetic device can be configured to accommodate the vessel at a pre-determined location. The kits provided herein can further contain a device for detecting the movement of a magnetic particle located in the vessel. In the kits provided herein, the device for detecting can be a magnetic plate. In the kits provided herein, the device for detecting can be configured to accommodate the vessel at a pre-determined location. The kits provided herein can further contain a magnetic device for moving and detecting the movement of a magnetic particle located in the vessel. In the kits provided herein, the device for moving and detecting can be a magnetic plate. In the kits provided herein, the device for moving and detecting can be configured to accommodate the vessel at a pre-determined location. The kits provided herein can further contain a fluid dispensing device. In the kits provided herein, the fluid dispensing device can be selected from the group consisting of a disposable pipette, an adjustable pipette, a fixed volume capillary pipette. The kits provided herein can further contain normal human plasma.

Also provided herein are methods for preparing a blood coagulation assay composition, by placing Factor X compound into a vessel and placing Factor V compound into the vessel. In the methods provided herein, any liquid placed into the vessel can be flash frozen upon placement into the vessel. In some methods provided herein, Factor X compound and Factor V compound are not simultaneously present in the vessel in aqueous liquid phase. In some methods provided herein, when Factor X compound and Factor V compound are simultaneously present in the vessel, at least one of Factor X compound and Factor V compound is not in contact with liquid phase $H_2O$. In some methods provided herein, when Factor X compound and Factor V compound are simultaneously present in the vessel, $H_2O$, when present in the vessel for more than an instant, is present in substantially only solid phase after the instant. In some methods provided herein, when Factor X compound and Factor V compound are simultaneously present in the vessel, at least one of Factor X compound and Factor V compound is not in contact with liquid phase $H_2O$. In some methods provided herein, the liquid phase is resultant from condensation of gaseous $H_2O$. In some methods provided herein, Factor X compound and Factor V compound are not simultaneously present in the vessel in aqueous liquid phase. In some methods provided herein, when Factor X compound and Factor V compound are simultaneously present in the vessel, $H_2O$, when present in the vessel for more than an instant, is present in substantially only solid phase after the instant. In some methods provided herein, when Factor X compound and Factor V compound are simultaneously present in the vessel, $H_2O$, when present in the vessel for more than an instant, is present in substantially only solid phase after the instant. In some methods provided herein, Factor X compound and Factor V compound are not simultaneously present in the vessel in aqueous liquid phase. In some methods provided herein, when Factor X compound and Factor V compound are simultaneously present in the vessel, at least one of Factor X compound and Factor V compound is not in contact with liquid phase $H_2O$. The methods provided herein can further include placing an additional component into the vessel, wherein the additional component can be selected from the group consisting of multivalent cation, lipid or detergent, fibrinogen, prothrombin complex, anticoagulant, normal plasma, and combinations thereof. In some methods provided herein, substantially no Factor II present in the vessel is converted to Factor $II_a$. In some methods provided herein, substantially no fibrinogen present in the vessel is converted to fibrin. Some methods provided herein can further include placing a plasma fraction into the vessel. In some methods provided herein, Factor V compound is a component of a plasma fraction. Some methods provided herein can further include placing a plasma fraction plasma fraction substantially free of Factors II, VII, IX, X into the vessel. In some methods provided herein, Factor X compound and a multivalent cation are present in a single mixture that is placed into the vessel. In some methods provided herein, Factor V compound and lipid or detergent are present in a single mixture that is placed into the vessel. In some methods provided herein, Factor V compound, lipid or detergent, and fibrinogen are present in a single mixture that is placed into the vessel. In some methods provided herein, Factor V compound, lipid or detergent, fibrinogen, and benzamidine are present in a single mixture that is placed into the vessel. In some methods provided herein, Factor V compound, lipid or detergent, anticoagulant, prothrombin complex, and normal plasma are present in a single mixture that is placed into the vessel. In some methods provided herein, Factor V compound, lipid or detergent, anticoagulant, prothrombin complex, normal plasma, and benzamidine are present in a single mixture that is placed into the vessel. In some methods provided herein, Factor V compound, lipid or detergent, anticoagulant, normal plasma, fibrinogen and benzamidine are present in a single mixture that is placed into the vessel. In some methods provided herein, Factor V compound, lipid or detergent, anticoagulant, antithrombin-III, Factor II, fibrinogen and benzamidine are present in a single mixture that is placed into the vessel. In some methods provided herein, the Factor X compound is Factor $X_a$. In some methods provided herein, the Factor V compound is Factor V. Also provided herein are compositions made by any of the methods provided herein. Such compositions can be present in combinations, such as combinations of a composition and a vessel. Such combinations can be present in kit form.

Also provided herein are methods of assaying coagulation of a sample, by mixing a sample with a coagulation assay composition and determining the time period beginning upon mixing and ending upon clot formation. The methods of assaying provided herein can include mixing a sample with a coagulation assay composition, combination or kit provided herein, and determining the time period beginning upon mixing and ending upon clot formation. The methods of assaying provided herein can include mixing a sample with a coagulation assay composition provided herein, and determining the time period beginning upon mixing and ending upon clot formation. The methods of assaying provided herein also can include adding blood directly into a clot monitoring vessel, mixing the blood with a coagulation assay composition, and determining the time period beginning upon mixing and ending upon clot formation. In the assay methods provided herein, the sample can be selected from the group consisting of a blood sample and a plasma sample. In the assay methods provided herein, the amount of a coagulation inhibitor in the sample can be determined. In the assay methods provided herein, the sample can be blood collected from a subject, and the amount of coagulation inhibitor in the subject's blood can be determined. In the assay methods provided herein, the time period can correlate linearly with the concentration of anticoagulant in the sample. In the assay methods provided herein, the time period can correlate linearly with a concentration range of heparin in the sample, wherein the heparin concentration range is selected from the group consisting of 0 units/mL to about 20 units/mL, 0 units/mL to about 15 units/mL, 0 units/mL to about 12 units/mL, 0 units/mL to about 10 units/mL, 0 units/mL to about 7.5 units/mL, and 0 units/mL to about 5 units/mL. In the assay methods provided herein, the time period can correlate linearly with a concentration range of hirudin in the sample, wherein the hirudin concentration range is selected from the group consisting of 0 µg/mL to about 20 µg/mL, 0 µg/mL to about 15 µg/mL, 0 µg/mL to about 12 µg/mL, 0 µg/mL to about 10 µg/mL, 0 µg/mL to about 7.5 µg/mL, and 0 µg/mL to about 5 µg/mL. In the assay methods provided herein, the time period can correlate linearly with a concentration range of heparin in the sample, wherein the heparin concentration range is selected from the group consisting of 0 units/mL to 20 units/mL, 0 units/mL to 15 units/mL, 0 units/mL to 12 units/mL, 0 units/mL to 10 units/mL, 0 units/mL to 7.5 units/mL, and 0 units/mL to 5 units/mL. In the assay methods provided herein, the time period can correlate linearly with a concentration range of hirudin in the sample, wherein the hirudin concentration range is selected from the group consisting of 0 µg/mL to 20 µg/mL, 0 µg/mL to 15 µg/mL, 0 µg/mL to 12 µg/mL, 0 µg/mL to 10 µg/mL, 0 µg/mL to 7.5 µg/mL, and 0 µg/mL to 5 µg/mL.

BRIEF DESCRIPTION OF THE DRAWINGS

FIG. 2 is a diagram depicting exemplary components of coagulation assay compositions and steps for forming such compositions.

DETAILED DESCRIPTION

Figure 1:
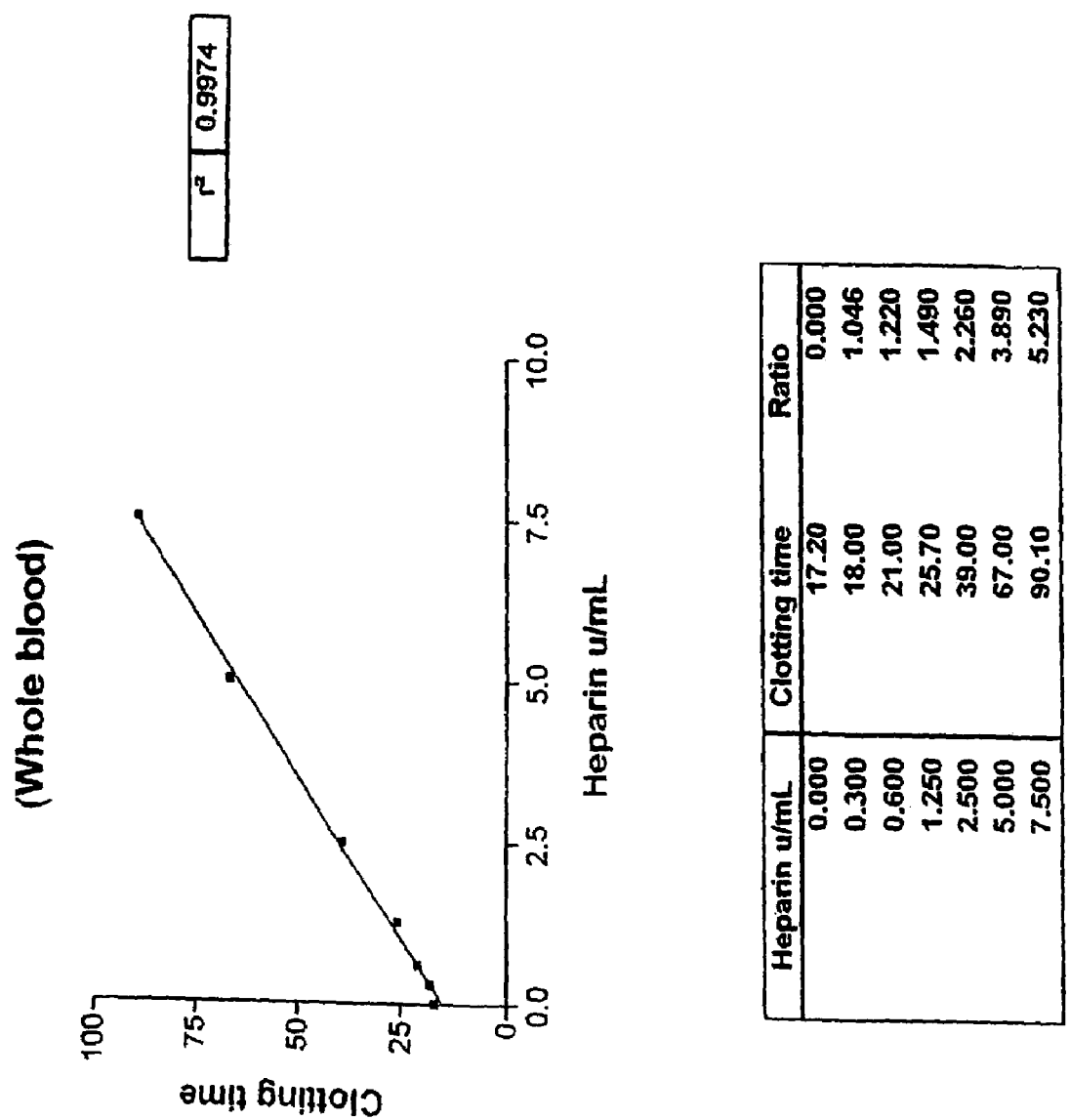
FIG. 1 is a linear curve depicting the linear relationship between clotting time and heparin concentration in normal human whole blood.

I. Compositions and Methods for Measuring Anticoagulants

The compositions, combinations and methods provided herein can be used to detect inhibitors of blood clot formation, such as anticoagulants in the blood, and also can be used to detect other blood components related to blood clotting, including blood components that promote or cause blood clotting. The compositions, combinations and methods provided herein also can be used to provide results that accurately reflect the quantity of anticoagulants in the blood. For example, the compositions, combinations and methods provided herein also can be used to detect compounds with anti-Factor $X_a$ and/or anti Factor $II_a$ activity, such as heparin.

Provided herein are blood coagulation assay compositions containing all components for performing a blood coagulation assay. The compositions can be used to perform simple, short, one-step blood coagulation assays. Blood coagulation assay compositions provided herein contain a Factor X compound such as Factor X or Factor $X_a$, and also contain a Factor V compound such as Factor V or Factor $V_a$. Some compositions provided herein can further contain additional components such as multivalent cation, lipid or detergent, plasma, fibrinogen, a plasma fraction containing fibrinogen, including a plasma fraction containing fibrinogen and Factor V compound, and combinations thereof. Plasma fractions can include a plasma fraction substantially free of Factors II, VII, IX, and X. Some blood coagulation assay compositions provided herein can further contain Factor II, prothrombin complex, or antithrombin III. The multivalent metal can be, for example calcium chloride or magnesium chloride, and lipid or detergent can be either from a natural source or synthetic. Also provided herein are combinations and kits that can contain, in addition to the blood coagulation assay composition, an anticoagulant, a blood collection device, a vessel for performing the assay, a mixing device, and a coagulation monitoring device.

Also provided herein are methods for preparing blood coagulation assay compositions, where two or more of the components of the assay are combined in such a way that they do not substantially react with one another. For example, the components can be combined in a vessel such that not all components are simultaneously present in the vessel in aqueous liquid phase. Methods for assaying coagulation of blood are also included, where the methods include adding blood or a blood sample to a vessel containing a coagulation assay composition, and determining the time period beginning upon addition of the blood or blood sample to the composition, and terminating at an endpoint such as clot formation. The determined time period can be used to accurately estimate the amount of anticoagulant in the sample. For example, the time period can be a direct function of the amount of anticoagulant in the sample.

II. Definitions

Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, anticoagulant refers to a compound that suppresses or inhibits coagulation or clot formation. Exemplary anticoagulants include compounds with anti-Factor $X_a$ and/or anti Factor $II_a$ activity, such as heparin or hirudin.

As used herein, heparin includes heparin molecules of a wide range of molecular weights, including low molecular weight heparins.

As used herein, a sample refers to a biological fluid from a subject that contains one or more compounds that influence blood coagulation. Exemplary samples include, but are not limited to, blood, plasma, serum, interstitial fluid, and lymph.

A subject can include any organism containing clotting factors, including avian, reptilian, amphibian, mammalian such as canine, feline, bovine, equine, porcine, rodent, ovine, caprine, and primate, where an exemplary primate is human.

As used herein, plasma refers to the acellular fluid in which blood cells are suspended. Plasma can be from any of a variety of biological subjects, where exemplary plasma is from a mammal such as canine, feline, bovine, equine, porcine, rodent, ovine, caprine or primate. Exemplary plasma sources are bovine and human.

As used herein, a Factor X compound refers to a compound that has Factor $X_a$ activity or can be activated to have Factor $X_a$ activity. Activation can take place by any known process, including proteolysis. An exemplary compound that has Factor $X_a$ activity is Factor $X_a$. An exemplary Factor X compound that can be activated to have Factor $X_a$ activity is Factor X.

As used herein, a Factor V compound refers to a compound that has Factor $V_a$ activity or can be activated to have Factor $V_a$ activity. Activation can take place by any known process, including proteolysis. An exemplary compound that has Factor $V_a$ activity is Factor $V_a$. An exemplary Factor V compound that can be activated to have Factor $V_a$ activity is Factor V.

As used herein, substantially, when used as a modifier of a term, refers to a state in which the functional properties of the term are not influenced beyond normal tolerance permitted by one skilled in the art. Thus, a first compound or composition that is substantially free of a second compound or composition refers to a first compound or composition whose functional properties are not influenced by the second compound or composition beyond normal tolerance permitted by one skilled in the art. For example, a composition that is substantially free of a blood clotting factor such as Factors II, VII, IX or X, refers to a composition having no such identified blood clotting factor, or so low an amount of such identified blood clotting factor as to not influence the functional properties of the composition beyond normal tolerance permitted by one skilled in the art. Typically, a first compound or composition that is substantially free of a second compound or composition refers to a first compound or composition that contains no more than about 25%, no more than about 20%, no more than about 10%, no more than about 5%, no more than about 3%, no more than about 2%, no more than about 1%, no more than about 0.5%, no more than about 0.3%, no more than about 0.2% or no more than about 0.1% of the second compound or composition. In another example, a first compound or composition that is substantially free of a second compound or composition refers to a first compound or composition that contains no more than 25%, no more than 20%, no more than 10%, no more than 5%, no more than 3%, no more than 2%, no more than 1%, no more than 0.5%, no more than 0.3%, no more than 0.2% or no more than 0.1% of the second compound or composition. Similarly, a vessel that contains substantially none of a particular compound or composition is a vessel whose one or more components are substantially free of the particular compound or composition. Similarly, a compound or composition that is substantially unreacted refers to a compound or composition whose functional properties are not changed, relative to a completely unreacted compound or composition, beyond normal tolerance permitted by one skilled in the art. For example, a composition that is substantially unreacted, refers to a composition in which the components are completely unreacted, or the components have reacted at so low of an amount that the functional properties of the composition are not influenced beyond normal tolerance permitted by one skilled in the art. Typically, a compound or composition that is substantially unreacted refers to a compound or composition in which no more than about 25%, no more than about 20%, no more than about 10%, no more than about 5%, no more than about 3%, no more than about 2%, no more than about 1%, no more than about 0.5%, no more than about 0.3%, no more than about 0.2% or no more than about 0.1% of the compound or composition is reacted. In another example, a compound or composition that is substantially unreacted refers to a compound or composition in which no more than 25%, no more than 20%, no more than 10%, no more than 5%, no more than 3%, no more than 2%, no more than 1%, no more than 0.5%, no more than 0.3%, no more than 0.2% or no more than 0.1% of the compound or composition is reacted. In instances where the amount of unreacted compound or composition is difficult to measure, a substantially unreacted compound or composition can be one in which one or more properties of the compound or composition are at least about 80%, at least about 90%, at least about 95%, at least about 98%, or at least about 99% the same as completely unreacted compound or composition, or at least 80%, at least 90%, at least 95%, at least 98%, or at least 99% the same as completely unreacted compound or composition. Exemplary properties include clotting time for a particular sample, for example, normal human plasma; slope of plot of clotting time versus anticoagulant concentration in, for example, a calibration curve; and range of anticoagulant concentration, such as heparin concentration, for which clotting time and anticoagulant concentration have a linear relationship. Similarly, a compound or composition in which substantially all of the compound or composition has a particular property refers to a compound or composition whose functional properties are not influenced by an amount of compound or composition that does not have the particular property, beyond normal tolerance permitted by one skilled in the art. For example, a composition that is substantially aqueously soluble refers to a compound or composition that is completely aqueously soluble, or a compound or composition in which so low an amount is not aqueously soluble that the functional properties of the composition are not changed beyond normal tolerance permitted by one skilled in the art. Typically, a compound or composition in which substantially all of the compound or composition has a particular property refers to a compound or composition in which no more than about 25%, no more than about 20%, no more than about 10%, no more than about 5%, no more than about 3%, no more than about 2%, no more than about 1%, no more than about 0.5%, no more than about 0.3%, no more than about 0.2% or no more than about 0.1% of the compound or composition does not have that property, or no more than 25%, no more than 20%, no more than 10%, no more than 5%, no more than 3%, no more than 2%, no more than 1%, no more than 0.5%, no more than 0.3%, no more than 0.2% or no more than 0.1% of the compound or composition does not have that property.

As used herein, composition refers to a substance containing two or more components. The term composition used herein does not require that the two or more components be admixed.

For clarity of disclosure, and not by way of limitation, the detailed description is divided into the subsections that follow.

III. Components of the Compositions

The compositions provided herein can be used in assaying coagulation of blood. The compositions provided herein contain a Factor X compound such as Factor X or Factor $X_a$, and also contain a Factor V compound such as Factor V or Factor $V_a$. The compositions also can include a variety of additional components, including a multivalent cation, lipid or detergent, fibrinogen, antithrombin III, and plasma or a plasma fraction. In embodiments in which one component of the composition contains multiple substances, such as embodiments in which one component of the composition is plasma or a plasma fraction containing multiple substances, one or more of: Factor X or Factor $X_a$, Factor V or Factor $V_a$, multivalent cation, lipid or detergent, fibrinogen, antithrombin III, or other intended component, can be one of the substances included in the plasma or plasma fraction. In such embodiments, inclusion of plasma or the particular plasma fraction can sufficiently contribute one of the specified components to the composition, and separate addition of such a component, is optional, according to the intended concentration of components of the composition. For example, when the composition contains a plasma fraction that includes a Factor V compound, separate addition of a Factor V compound to the composition is not required, but can be accomplished if desired. Thus, a variety of sources of the components are possible in constructing the compositions provided herein. One skilled in the art can determine according to the teachings provided herein and the general knowledge in the art any of a variety of different mixtures that can be used to arrive that the compositions provided herein.

A. Factor X Compound

The compositions provided herein can contain a Factor X compound, such as Factor X or Factor $X_a$. Factor $X_a$ is an activated form of Factor X. Factor X can be activated by any of a variety of agents known in the art, including, but not limited to Russels viper venom, thromboplastin, and citrate. In one embodiment, the compositions provided herein can contain Factor X. In another embodiment, the compositions provided herein can contain Factor $X_a$. Composition embodiments that contain Factor X can also contain one or more Factor X-activating agents, such as Russels viper venom. Factor X compounds can be obtained from any of a variety of sources, as known in the art. For example Factor X compounds can be prepared from plasma, such as bovine plasma, as known in the art and exemplified in Yin et al., J. Biol. Chem. 243:112 (1968). Factor X compounds also can be obtained in partially or substantially purified form from a variety of commercial sources. For example, substantially pure Factor $X_a$ in lyophilized form is available from Heptest Laboratories (St. Louis, Mo.).

1. Factor X Compound in a Composition

Factor X compound can be provided in solid form, such as lyophilized form, or can be provided in solution, for example, in an aqueous solution. Factor X compound can be present in a composition such as a fluid containing one or more additional components. Factor X compound also can be present in a composition such as a solid containing one or more additional components. As contemplated herein, the Factor X compound-containing compositions described herein as fluids also can be present in solid form (e.g., frozen or lyophilized form). Accordingly, one skilled in the art will understand that reference herein to components that can be present in a Factor X compound-containing fluid composition also includes reference to components that can be present in a Factor X compound-containing solid composition. In one example, Factor X compound can be present in a composition such as a fluid that also contains one or more buffering solution components. Exemplary buffering solution components include buffering compound, salt, and additional components for stabilizing components of the Factor X compound-containing composition and for facilitating solubilization of components of the Factor X compound-containing composition, such as lactose, bovine serum albumin (BSA), and polyethylene glycol.

Buffering compounds can be any of a variety of compounds known in the art for stabilizing pH in a range suitable for Factor X or Factor $X_a$, including amine, imine, phosphate, and sulfate based buffering compounds, such as tris-maleate or tris-HCl. Ranges of pH suitable for Factor X compound-containing solutions are approximately 5 to 8, typically 7.0 to 8.0. An exemplary buffering compound is Tris hydroxymethyl aminomethane maleate at pH 7.5. Buffering compounds can be present at any concentration that provides the desirable level of pH buffering, such as 5 mM-500 mM. An exemplary concentration for buffering compound is 100 mM.

Salts can be any of a variety of compounds known in the art as suitable in solution with Factor X or Factor $X_a$, including, but not limited to NaCl, NaCitrate, $CaCl_2$ and $MgCl_2$. Any of a variety of salts can be present, including a combination of salts containing monovalent ions and salts containing multivalent ions such as divalent ions. Ranges of salt concentrations for Factor $X_a$ solutions are approximately 10 mM to 200 mM, typically 50 mM to 200 mM. An exemplary salt compound and concentration is NaCl at 150 mM. Multivalent salts such as divalent salts can be present in addition to salts such as NaCl. Typically a multivalent salt contains a multivalent cation, such as a divalent cation, including $Ca^{2+}$ and $Mg^{2+}$. An exemplary multivalent salt compound and concentration is $CaCl_2$ at 25 to 50 mM, typically about 25 mM or 50 mM, or 25 mM or 50 mM.

A composition containing Factor X compound can also contain one or more stabilizers, as known in the art. Stabilizers can aid in preserving the activity of components such as Factor X or Factor $X_a$ in the composition. While not intending to be limited by the following, stabilizers can act by preventing proteins such as Factor X or Factor $X_a$ from losing activity by, for example, adsorption onto a surface such as glass or plastic. A variety of stabilizers is known in the art, and includes, for example bovine serum albumin (BSA) and polyethylene glycol (PEG). Exemplary concentrations of stabilizers include BSA ranging from about 0.5% to about 1.0%, typically about 1%, and PEG ranging from about 0.5% to about 1.0%, typically about 1%. Additional exemplary concentrations of stabilizers include BSA ranging from 0.5% to 1.0%, typically 1%, and PEG ranging from 0.5% to 1.0%, typically 1%. Additional exemplary concentrations of stabilizers include BSA ranging from about 0.5% to about 5.0%, typically about 3%, and PEG ranging from about 0.05% to about 0.5%, typically about 0.1%. Additional exemplary concentrations of stabilizers include BSA ranging from 0.5% to 5.0%, typically 3%, and PEG ranging from 0.05% to 0.5%, typically 0.1%.

A composition containing Factor X compound can also contain one or more compounds that facilitate solubilization. When Factor X compound is present in solvent-free form (e.g., in lyophilized form), one or more compounds can be used that facilitate solvent-free Factor X compound to dissolve upon contact with an appropriate solvent such as liquid $H_2O$ or a liquid aqueous solution. Any of a variety of solubilizing compounds known in the art can be used, including, but not limited to, lactose. Exemplary concentrations of solubilizing compounds include lactose ranging from about 1.0% to about 20%, typically about 5 or about 10%. Additional exemplary concentrations of solubilizing compounds include lactose ranging from 1.0% to 20%, typically 5 or 10%.

In addition, glycine can be added to a composition containing Factor X compound. Exemplary concentrations of glycine can range from about 0.5% to about 2%, typically about 1%. Additional exemplary concentrations of glycine can range from 0.5% to 2%, typically 1%.

In another embodiment, a composition such as a fluid composition can contain Factor X compound and one or more compounds that are active in a blood clotting assay, including but not limited to, a blood clotting enzyme, a substrate of a blood clotting enzyme, a modulator of blood clotting enzyme activity (e.g., an inhibitor or activator), and combinations thereof. Exemplary compounds that can be in a composition such as a fluid composition with Factor X compound include, but are not limited to, multivalent cation, lipid or detergent, fibrinogen, and combinations thereof. Additional components that can be added to a composition containing Factor X compound include Factor II, prothrombin complex, and combinations thereof. Factor $X_a$ is typically not provided in fluid solution with antithrombin III. Further, in some embodiments, Factor X compound is not provided in fluid solution with Factor V compound.

B. Factor V Compound

The composition provided herein can contain Factor V compound. Factor V compound can include Factor V and Factor $V_a$, and can be obtained by any of a variety of methods known in the art, as exemplified in Dahlback, J Clin Invest. 66:583-91 (1980), Kane, et al., J. Biol. Chem. 256:1002-1007 (1981), Smirnov et al., J Biol Chem 273: 9031-9040 (1998), U.S. Pat. No. 4,851,336 to Yin, and U.S. Pat. Pub. No. 20030104508. For example, a Factor V-containing plasma fraction can be prepared from plasma, such as bovine plasma, as known in the art and exemplified in U.S. Pat. No. 4,851,336 to Yin. Factor V is also available from commercial suppliers, including CalBiochem (San Diego, Calif.). Methods also are known in the art for activating Factor V to Factor $V_a$. The methods and commercial sources can be used to obtain Factor V compound in partially purified form or substantially purified form.

1. Factor V Compound Composition

Factor V compound can be provided in solid form, such as lyophilized form, or can be provided in solution, for example, in an aqueous solution. Factor V compound can be present in a composition such as a fluid containing one or more additional components. Factor V compound also can be present in a composition such as a solid containing one or more additional components. As contemplated herein, the Factor V compound-containing compositions described herein as fluids also can be present in solid form (e.g., frozen or lyophilized form). Accordingly, one skilled in the art will understand that reference herein to components that can be present in a Factor V compound-containing fluid composition also includes reference to components that can be present in a Factor X compound-containing solid composition. In one example, Factor V compound can be present in a composition such as a fluid composition containing one or more buffering solution components. In another example, Factor V compound can be present in a biological fluid or a fraction thereof. In another example Factor V compound can be in a composition containing one or more additional components of a coagulation assay composition.

a. Buffer Conditions

Factor V compound can be present in a composition such as a fluid that also contains one or more buffering solution components, as known in the art. Exemplary buffering solution components include buffering compound, salt, stabilizers and solubilizers, as described herein for compositions containing Factor X compound.

Factor V compound buffer conditions can vary as desirable for desired properties. For example, salt concentration, such as sodium chloride concentration can be about 250 mM to about 750 mM, such as about 500 mM. In another example, salt concentration, such as sodium chloride concentration can be 250 mM to 750 mM, such as 500 mM. In another example, PEG can be present at about 0.1% to about 1%, such as about 0.25%. In another example, BSA can be present at about 1% to about 10%, such as about 4%. In another example, PEG can be present at 0.1% to 1%, such as 0.25%. In another example, BSA can be present at 1% to 10%, such as 4%. In another example, compounds such as multivalent cation salt, lactose and glycine are not added to the Factor V compound solution.

b. Factor V Compound with other Components

Factor V compound also can be provided as one component of a composition such as a fluid composition of substances, for example, in a biological fluid such as plasma or a plasma fraction. In one embodiment, such a composition can contain Factor V compound and one or more additional blood components. In another embodiment, Factor V compound can be in a composition containing fibrinogen, or a composition containing antithrombin III, or a composition containing both antithrombin III and fibrinogen. In another embodiment, Factor V compound can be in a composition containing lipid or detergent, normal plasma, prothrombin complex, anticoagulant, or combinations thereof.

One example of a plasma fraction containing Factor V compound is a plasma fraction that contains Factor V and, optionally, fibrinogen, and is substantially free of Factors II, VII, IX and X. Methods for preparing such a plasma fraction are known in the art, as exemplified in U.S. Pat. No. 4,851,336. An exemplary method for producing such a plasma fraction can be performed by treating mammalian blood with a coagulation suppressing composition, and then removing blood cells to produce plasma, then treating the plasma with at least one separation step to remove coagulation Factors II, VII, IX and X, then treating the resulting plasma fraction with any further desired separation steps and recovering therefrom a protein fraction containing coagulation Factor V and optionally fibrinogen, and then treating the protein fraction to remove therefrom soluble ammonium salt and insoluble proteins. The resultant plasma fraction can be buffered and can also be admixed with one or more compounds, such as fibrinogen, lipid or detergent, prothrombin complex, anticoagulant, normal plasma, or combinations thereof.

Each of the steps of the exemplary protocol can be performed by any of a variety of methods known in the art, as exemplified in U.S. Pat. No. 4,851,336. Brief descriptions of exemplary methods for performing each step are as follows. In the blood treatment step, blood can be treated with any of a variety of coagulation suppressing compounds or compositions, as known in the art, for example, a 3.8% sodium citrate solution, a sodium or potassium oxalate solution, or EDTA. Typically, when a sodium citrate solution is used, it is mixed with blood in ratios of about 9:1 blood:sodium citrate, or ratios of 9:1 blood:sodium citrate. The treated blood can then be treated in one or more steps to separate blood cells from the plasma, as known in the art. For example, the treated blood can be centrifuged at 2500×g for 15 minutes. The resultant plasma can then be used in subsequent treatment steps.

The plasma can be treated to separate Factors II, VII, IX and X from Factor V. Any of a variety of separation methods can be used to perform this step, as known in the art, including, but not limited to, liquid chromatographic methods such as affinity chromatography, ion exchange chromatography, or gel filtration chromatography, and precipitation methods including salt precipitation or alcohol precipitation. In some embodiments, fibrinogen can also be present in the fraction containing Factor V. In an exemplary method, the plasma can be treated to have Factors II, VII, IX and X become no longer dissolved in the plasma solution while Factor V, and, optionally, fibrinogen, remain dissolved. Any of a variety of precipitation methods known for removing Factors II, VII, IX and X from the plasma solution while Factor V, and, optionally, fibrinogen, remains dissolved, can be used. In an exemplary method, 1 liter of plasma can have dissolved therewith 7.35 g of trisodium citrate, followed by addition of 20.825 g of barium chloride (to achieve an overall barium chloride concentration of about 0.1 M in the plasma mixture) at room temperature over a period of 1-2 hours. Methods using solutions containing citrate and barium ions as precipitants can be performed at any of a variety of citrate and barium ion concentrations known to remove Factors II, VII, IX and X from the plasma solution, without also substantially removing Factor V, and, optionally, fibrinogen, from the plasma solution, as known in the art. As an alternate example, when the blood from the first step of plasma isolation is treated with a coagulation suppressor such as sodium or potassium oxalate, the plasma treatment step can include treating the plasma with barium sulfate, which can result in Factors II, VII, IX and X being removed from the plasma solution while Factor V, and, optionally, fibrinogen, remain dissolved. Methods for using barium sulfate to remove Factors II, VII, IX and X from plasma without substantially removing Factor V, and optionally, fibrinogen, are known in the art, as exemplified in page 592, Human Blood Coagulation, Haemostasis and Thrombosis, edited by Biggs, 1972. The resultant solid can then be separated from the liquid by any of a variety of methods known in the art, including, but not limited to, centrifugation and filtration. For example, centrifugation of the treated plasma can be performed, for example, at 3000×g for 20 minutes, where the resulting pellet plasma fraction typically contains Factors II, VII, IX and X, and the supernatant plasma fraction typically contains Factor V, and, optionally, fibrinogen. The Factor V-containing supernatant plasma fraction can then be further treated.

The supernatant plasma fraction can be treated by a further step in order to separate Factor V, and, optionally, fibrinogen, from other non-clotting proteins. Any of a variety of separation methods can be used to perform this step, such as chromatographic and precipitation methods, as provided herein or otherwise known in the art. In one exemplary method, the supernatant plasma fraction can be treated with a salt, such as ammonium sulfate, to precipitate the Factor V and any other intended components such as fibrinogen. The use of ammonium sulfate for the fractionation of Factor V is known in the art, as exemplified in "Human Blood Coagulation and Its Disorders" edited by Biggs & MacFarlane, p. 54, 3rd edition 1962. The use of ammonium sulfate to precipitate fibrinogen also is known in the art, as exemplified in "The Biochemistry of Blood Coagulation" by T. Astrup, in Acta Physiologica Scandanavia, Supplement 21, 1944. In an exemplary method, ammonium sulfate can be added to the supernatant plasma fraction at a concentration of about 270 g per liter or 270 g per liter of the plasma fraction, at room temperature, resulting in an about 40% to 45% or 40% to 45% saturated solution. Such mixture can be incubated at room temperature for 1-2 hours. Other salts or other ammonium sulfate concentrations can also be used to achieve similar results, as is known in the art. For example a saturated ammonium sulfate-plasma fraction can contain a range from about 30% to about 60% or 30% to 60% ammonium sulfate, typically from about 35% to about 50% or 35% to 50% ammonium sulfate. Generally in such methods, an ammonium sulfate concentration of about 30% or 30% saturation results in fibrinogen precipitation, and an ammonium sulfate concentration between about 30% or 30% saturation to about 40% or 40% saturation results in Factor V precipitation. The resultant precipitate of the mixture can be separated from the liquid by any of a variety of methods known in the art, such as centrifugation or filtration. For example, the mixture can be centrifuged at 4000×g for 15 minutes at room temperature. Typically for an ammonium sulfate precipitation such as that presented in this paragraph, the fraction containing Factor V, and optionally, fibrinogen, is the precipitate, which forms a pellet upon centrifugation.

The pellet plasma fraction can then be resuspended in an aqueous solution, as known in the art. The aqueous solution can be of any volume or composition suitable for stabilizing Factor V and other intended components of the pellet, such as, but not limited to, fibrinogen. For example, the pellet can be resuspended in a volume of distilled water equal to 30-40% of the original plasma volume. The resuspended pellet plasma fraction can then be treated to remove ammonium ion from the solution. Removal of solutes including ions such as ammonium from a solution can be accomplished by any of a variety of methods known in the art, typically by use of a membrane for filtration and/or solute/solvent exchange. An exemplary method is dialysis. For example, the resuspended pellet plasma fraction can be dialysed against a 0.9% NaCl solution or equivalent, including tap water. Typically, such solute removal steps are performed by adding barium chloride to a sample of the dialysis solution and monitoring for the precipitation of barium sulfate. When precipitate is no longer formed, solute exchange is sufficiently complete.

After solute exchange such as dialysis, the resuspended pellet plasma fraction can be treated in one or more steps to have any solids or particulate matter removed. Any of a variety of methods known in the art for removing solids from a solution can be used, including centrifugation or filtration. For example, the mixture can be centrifuged at 3000×g for 15 minutes at room temperature.

The plasma fraction resultant from the above procedure or equivalents thereof known in the art, can then have added thereto one or more buffering solution components, including, but not limited to, buffering compounds, salts, bovine serum albumin (BSA), lactose, and polyethylene glycol. Such buffering solution components are further described herein elsewhere. An exemplary buffering solution can contain 2.50 g polyethyleneglycol, 9.0 g NaCl, 98.88 g Tris-maleate, and 100 g lactose per liter of distilled water, at a pH of 7.5, where the buffering solution is combined with the plasma fraction at a ratio of 9:1 plasma fraction:buffering solution.

The buffered plasma fraction can also have added thereto lipid or detergent such as brain phospholipids including cephalin. The amount of added lipid or detergent can be a function of the concentration of Factor X compound selected for the assay. For example, the more concentrated the Factor X compound present in the assay system, the less amount of lipid added to the Factor V-containing composition. The resulting plasma fraction admixture can be described in terms of one or more of its components, in terms of one or more steps in its method of preparation, or in terms of one or more of its properties. However, regardless of the manner described, one skilled in the art, based on the teachings provided herein and the knowledge of skill in the art, will recognize that a range of related plasma fraction products can contain the intended components and intended amounts in suitable form for use in the methods and compositions provided herein.

The resultant plasma fraction is characterized as containing Factor V. The Factor V-containing plasma fraction can also, optionally be characterized by one or more additional properties, including, but not limited to: it contains fibrinogen, it does not clot by itself for at least 24 hours at 37° C., it can form a firm clot in the presence of added thrombin, it contains at least 25% of Factor V that is present per unit volume in normal human plasma, and it can be used in a coagulation assay to provide a linear anticoagulant curve using a standard anticoagulant preparation, such as a standard heparin preparation.

2. Optional Components

In another embodiment, a composition such as a fluid composition can contain Factor V compound and one or more compounds that are active in a blood clotting assay, including but not limited to, a blood clotting enzyme, a substrate of a blood clotting enzyme, a modulator of blood clotting enzyme activity (e.g., an inhibitor or activator), and combinations thereof. Exemplary compounds that can be in a composition with Factor V compound include, but are not limited to lipid or detergent, fibrinogen, antithrombin III, Factor II, prothrombin complex, anticoagulant, normal plasma, and combinations thereof. For example, Factor V compound or a plasma fraction containing Factor V compound can further contain lipid or detergent. In another example, a Factor V compound or a plasma fraction containing Factor V compound can further contain fibrinogen. In another example, Factor V compound or a plasma fraction containing Factor V compound can further contain antithrombin III. In another example, Factor V compound or a plasma fraction containing Factor V compound can further contain Factor II. In another example, Factor V compound or a plasma fraction containing Factor V compound can further contain prothrombin complex. In another example, Factor V compound or a plasma fraction containing Factor V compound can further contain normal plasma. In another example, Factor V compound or a plasma fraction containing Factor V compound can further contain anticoagulant. In another example, Factor V compound or a plasma fraction containing Factor V compound can further contain combinations of two or more of lipid or detergent, fibrinogen, antithrombin III, factor II, prothrombin complex, normal plasma, and anticoagulant. In another example, a composition containing Factor V compound and fibrinogen or a plasma fraction containing Factor V compound and fibrinogen can further contain lipid or detergent. In another example, a composition containing Factor V compound and fibrinogen or a plasma fraction containing Factor V compound and fibrinogen can further contain antithrombin III. In another example, a composition containing Factor V compound and fibrinogen or a plasma fraction containing Factor V compound and fibrinogen can further contain Factor II or prothrombin complex. In another example, a composition containing Factor V compound and fibrinogen or a plasma fraction containing Factor V compound and fibrinogen can further contain normal plasma. In another example, a composition containing Factor V compound and fibrinogen or a plasma fraction containing Factor V compound and fibrinogen can further contain anticoagulant. In another example, a composition containing Factor V compound and fibrinogen or a plasma fraction containing Factor V compound and fibrinogen can further contain two or more of phospholipid or detergent, antithrombin III, Factor II, prothrombin complex, normal plasma, and anticoagulant. In one example, a composition containing Factor V compound, such as a plasma fraction containing Factor V compound, can further contain lipid or detergent, normal plasma, prothrombin complex, and anticoagulant.

C. Additional Components

The coagulation assay compositions provided herein can include components in addition to Factor X compound and Factor V compound. As provided herein, additional components can be biological compositions such as normal plasma, or can be blood clotting factors such as fibrinogen, prothrombin complex, Factor II or antithrombin III, or other components that influence clotting such as anticoagulant, multivalent cations, and lipid or detergent.

Fibrinogen, prothrombin complex, Factor II, normal plasma, anticoagulant, and antithrombin III can readily be obtained by methods known in the art or by commercial sources.

When a multivalent cation salt and lipid or detergent are included, they can each be present in substantially pure form, or can be present in a composition such as a fluid composition, including a composition containing one or more components that are active in a blood clotting assay, including, but not limited to, a blood clotting enzyme, a blood clotting enzyme substrate, a blood clotting enzyme modulator, and combinations thereof. For example, multivalent cation salt and/or lipid or detergent can be in a composition such as a fluid composition with Factor $X_a$, Factor V, fibrinogen, normal plasma, prothrombin complex, anticoagulant, antithrombin III, and combinations thereof.

In some embodiments, when multivalent cation salt and lipid or detergent are added rapidly together in a fluid composition, precipitate may form. Accordingly, when multivalent cation salt and lipid or detergent are to be present in a fluid composition, they can be present in a fluid that also contains a compound or composition that suppresses precipitate formation. Compounds and compositions that suppress precipitate formation in fluids containing multivalent cation salt and lipid or detergent are known in the art. In one example, a plasma protein, such as BSA, can suppress precipitate formation in fluids containing multivalent cation salt and lipid or detergent. In another example, a plasma fraction can suppress precipitate formation in fluids containing multivalent cation salt and lipid or detergent. In another example a plasma fraction containing Factor V compound can suppress precipitate formation in fluids containing multivalent cation salt and lipid or detergent. When multivalent cation salt and lipid or detergent are to be added to a fluid, typically a first of the two is fully added and fully mixed prior to adding the second. In one example, multivalent cation salt is fully mixed into a fluid composition prior to adding lipid or detergent. An exemplary fluid into which multivalent cation salt and lipid or detergent can be mixed is a plasma fraction containing Factor V compound, such as a buffered plasma fraction containing Factor V compound, as provided herein or otherwise known in the art. Additional compounds and compositions which can be mixed with multivalent cation salt and/or lipid or detergent to form a composition such as a fluid composition, include, but are not limited to antithrombin III, Factor II, Factor X compound, fibrinogen, anticoagulant, normal plasma and prothrombin complex.

1. Multivalent Cation-Containing Salt

The salts used in the compositions provided herein can include any of a variety of salts containing multivalent cations that are known to promote coagulation. In one embodiment, the multivalent cation is a divalent cation. Any of a variety of divalent cations known to promote coagulation can be used, including, but not limited to, calcium ion and magnesium ion. Typically the counteranion of the cation can be any anion that does not inhibit coagulation. Any of a variety of anions can be used as the counteranion, as known in the art. Exemplary anions include halides, carboxylates, sulfates, sulfites, phosphates, nitrates, and nitrites. In one embodiment, divalent cation halides such as calcium chloride and magnesium chloride are used. Any of a variety of multivalent cation salts such as calcium salts is available from commercial sources, such as Sigma-Aldrich (St. Louis, Mo.).

In one embodiment, compositions provided herein also include any coagulation assay composition known in the art, including compositions not containing both Factor X compound and Factor V compound, or compositions not containing either Factor X compound or Factor V compound, having added thereto a multivalent cation. A variety of coagulation assay compositions are known in the art, and include ACT and APTT assay compositions, as exemplified in U.S. Pat. Nos. 6,699,718, 6,528,273 and 6,140,062. Multivalent cation, such as divalent cation including calcium and magnesium ions, can be present in such coagulation assay compositions, while the components of the coagulation assay compositions are substantially unreacted or unactivated. Multivalent cation, such as divalent cation including calcium and magnesium ions, can be present in such coagulation assay compositions, where the compositions are substantially free of liquid or gaseous $H_2O$.

2. Lipid or Detergent

The coagulation assay compositions provided herein also can include lipid or detergent. Typical lipid used include phospholipids such as phosphatidylcholine, phosphatidylserine, phosphatidylethanolamine, phosphatidylinositol, and cardiolipin. Phospholipids used in the compositions provided herein can include any phospholipid known to promote coagulation (i.e., any procoagulant phospholipid), including biological isolates containing phospholipids; for example, a typical phospholipid in the compositions provided herein is phospholipids from rabbit brain (e.g., cephalin). In another example, the phospolipid can be soybean phospholipid. Any of a variety of procoagulant phospholipids known in the art can be used, including, but not limited to, cephalins. Any of a variety of procoagulant phospholipids is available from commercial sources, such as Sigma-Aldrich (St. Louis, Mo.). Procoagulant phospolipids also can be isolated from biological sources according to any of a variety of methods known in the art. For example, brain phospholipids such as cephalin can be isolated from brain, as known in the art, and exemplified in Bell et al., Nature, 174:880 (1954). Exemplary brains for isolation of brain phospholipids such as cephalin are rabbit brain or bovine brain.

Detergent used in the compositions provided herein can include any detergent known to promote coagulation. Typical detergents used include cationic detergents such as CTAB (cetyltrimethyl-ammonium bromide). Exemplary detergents include, but are not limited to, CTAB and phosphatidic acid. Any of a variety of detergents is available from commercial sources, such as Sigma (St. Louis, Mo.).

Also encompassed within the use of lipid or detergent in the compositions provided herein are compositions containing two or more different lipids or detergents, which can include two or more different lipids, two or more different detergents, or combinations of at least one lipid and at least one detergent. Compositions containing two or more different lipids or detergents can be formed by combining two pure or substantially pure lipids or detergents, or can be biological isolates containing two or more lipids or detergents, such as a lipid isolate from a biological source containing two or more lipids or detergents; an exemplary biological isolate is a lipid isolate from brain, such as brain cephalin. A variety of mixtures of lipids, detergents, and lipids and detergents, are known in the art to have procoagulant activity. For example, phophatidylserine can be used in combination with CTAB. One skilled in the art will readily understand any of a variety of mixtures that can be used, as is well known and exemplified in publications such as Barton et al., J. Lipid Res. 11:87-95 (1970) and Papahadjoupolus et al., Proc. Soc. Exp. Biol. Med. 111:412 (1962).

D. Optional Components

The coagulation assay compositions provided herein can also contain a variety of additional components. Exemplary components are those that contain one or more compounds that are active in a blood clotting assay, including, but not limited to, a blood clotting enzyme, a blood clotting enzyme substrate, or a blood clotting enzyme modulator. Such components include, but are not limited to, normal plasma, prothrombin complex, Factor II, anticoagulant, and antithrombin III. As described elsewhere herein, any such additional component can be added with any of Factor X compound, Factor V compound, multivalent cation salt, or lipid or detergent, or with any composition containing Factor X compound, Factor V compound, multivalent cation salt, or lipid or detergent, such as a plasma fraction containing Factor X compound, Factor V compound, multivalent cation salt, or lipid or detergent. However, typically antithrombin III is not in fluid mixture with Faxtor $X_a$. In some embodiments, Factor X compound is not in fluid mixture with Factor V compound or a fluid composition containing Factor V compound.

E. Components when Combined

The components described herein can be combined to form the coagulation assay composition provided herein. Methods for combining the components are provided herein elsewhere. Typically, the coagulation assay compositions, when all components are combined, will contain substantially no $H_2O$ in liquid or gaseous form prior to use in performing a coagulation assay. While not intended to be limited to the following, when all components are present in a composition, and the composition contains a significant amount of $H_2O$ in liquid form (including condensate from $H_2O$ vapor), the components may react, degrade, or otherwise be modified to render the composition ineffective or undesirably less effective in coagulation assays. The compositions provided herein can include $H_2O$ in solid form, provided that, prior to use in performing the coagulation assay, the ambient conditions are not changed to a point in which $H_2O$ is in contact with the composition in liquid form, for example the ambient temperature of the composition is not raised to a temperature at which a substantial amount of $H_2O$ transitions to liquid or gaseous form.

In one embodiment, the coagulation assay compositions, when all components are combined, can also possess one or more additional characteristics. In one characteristic, the components of the composition can be present in substantially unreacted form. For example, components of the composition can be substantially unreacted with one another. In another characteristic, the components of the composition can be present in substantially unactivated form. For example, components of the composition can be in a state where any coagulation process is substantially unactivated. In another example, Factor X compound in the composition is substantially unbound by antithrombin III. In another characteristic, the composition is substantially free of products of a clotting reaction. For example, the composition can be substantially free of Factor $II_a$ and/or can be substantially free of fibrin. In another characteristic, substantially all of the Factor Xa of the composition is aqueously soluble. In another characteristic, substantially all of the calcium salt of the composition is aqueously soluble.

In another embodiment, the coagulation assay composition is characterized such that Factor X compound and Factor V compound are substantially not admixed. For example, Factor X compound can be in a solid form, and Factor V can be in solid form, where the Factor X compound solid can be attached to or in contact with the Factor V compound solid, but these solids are not substantially admixed.

In another embodiment, the coagulation assay composition is characterized such that Factor X compound is present in a discrete solid form and Factor V compound is present in a discrete solid form, and wherein the discrete solid form of Factor X compound contacts substantially only the surface of the discrete solid form of Factor V compound. In another embodiment, the coagulation assay composition is characterized such that Factor X compound is present in a discrete solid form and Factor V compound is present in a discrete solid form, and wherein the discrete solid form of Factor X compound contacts no more than substantially only the surface of the discrete solid form of Factor V compound. In another embodiment, the coagulation assay composition is characterized such that Factor X compound and Factor V compound are present in discrete separate portions, wherein the discrete separate portions contact substantially only the surface of one another. In another embodiment, the coagulation assay composition is characterized such that Factor X compound and Factor V compound are present in discrete separate portions, wherein the discrete separate portions contact nor more than substantially only the surface of one another. In another embodiment, the coagulation assay composition is characterized such that Factor X compound is admixed with at least one admixing compound, wherein the admixing compound is substantially not admixed with Factor V compound. In another embodiment, the coagulation assay composition is characterized such that Factor X compound is admixed with at least one admixing compound, wherein the admixing compound is substantially unreacted with Factor V compound. In another embodiment, the coagulation assay composition is characterized such that Factor V compound is admixed with at least one admixing compound, wherein the admixing compound is substantially not admixed with Factor X compound. In another embodiment, the coagulation assay composition is characterized such that Factor V compound is admixed with at least one admixing compound, wherein the admixing compound is substantially unreacted with Factor X compound. In another embodiment, the coagulation assay composition is characterized such that Factor V compound is not in fluid mixture with Factor V compound. In another embodiment, the coagulation assay composition is characterized such that Factor X compound is not in a fluid composition containing Factor V compound. In another embodiment, the coagulation assay composition is characterized such that wherein addition of an aqueous liquid to the composition causes Factor X compound and Factor V compound to become substantially admixed. In another embodiment, the coagulation assay composition is characterized such that Factor X compound is present in excess relative to the amount of sample to be added to the composition. In another embodiment, the coagulation assay composition is characterized such that Factor V compound is present in excess relative to the amount of sample to be added to the composition. In another embodiment, the coagulation assay composition is characterized such that multivalent cation salt is present in excess relative to the amount of sample to be added to the composition.

In another characteristic, the composition can have reactive properties, where, upon addition of blood or a blood sample to the composition, a clotting reaction initiates. In another characteristic, the composition can have reactive properties, where a measured clotting time can be used to determine the amount of anticoagulant, such as heparin, in the sample. In another characteristic, the composition can have reactive properties, where the amount of anticoagulant, such as heparin, in a sample containing anticoagulant amounts ranging from 0 units/mL to about 15 units/mL or from 0 units/mL to 15 units/mL, is linearly correlated with clotting time. In another characteristic, the composition can have reactive properties, where the amount of anticoagulant, such as heparin, in a sample containing anticoagulant amounts ranging from 0 units/mL to about 10 units/mL or 0 units/mL to 10 units/mL, is linearly correlated with clotting time. In another characteristic, the composition can have reactive properties, where the amount of anticoagulant, such as heparin, in a sample containing anticoagulant amounts ranging from 0 units/mL to about 7.5 units/mL or 0 units/mL to 7.5 units/mL, is linearly correlated with clotting time. In another characteristic, the composition can have reactive properties, where, upon addition of a normal blood sample or a normal plasma sample to the composition, a clotting reaction terminates within 60 seconds of addition of the sample. In another characteristic, the composition can have reactive properties, where, upon addition of a normal blood sample or a normal plasma to the composition, a clotting reaction terminates within 120 seconds of addition of the sample. In another characteristic, the composition can have reactive properties, where, upon addition of a normal blood sample or a normal plasma sample to the composition, a clotting reaction terminates within 300 seconds of addition of the sample. In another characteristic, the composition can have reactive properties, where, upon addition of a normal blood sample or a normal plasma to the composition, a clotting reaction terminates within 600 seconds of addition of the sample. In another embodiment, the composition can have reactive properties, wherein, upon addition of a normal plasma or blood sample, clotting time ranges from about 10 to about 13 seconds or 10 to 13 seconds, and, upon addition of a normal plasma or blood sample containing 3 units/mL of heparin, clotting time ranges from about 35 to about 50 seconds or 35 to 50 seconds. In another embodiment, the composition can have reactive properties, wherein, upon addition of a normal plasma or blood sample, clotting time ranges from about 15 to about 20 seconds or 15 to 20 seconds, and, upon addition of a normal plasma or blood sample containing 3 units/mL of heparin, clotting time ranges from about 40 to about 55 seconds or 40 to 55 seconds. In another embodiment, the composition can have reactive properties, wherein, upon addition of a normal plasma or blood sample, clotting time ranges from about 13 to about 17 seconds or 13 to 17 seconds, and, upon addition of a normal plasma or blood sample containing 7.5 units/mL of heparin, clotting time is less than about 100 seconds or 100 seconds. Any of a variety of additional combinations of components can be prepared to have related clotting time properties, according to the teachings provided herein and the desired properties of the composition.

In another characteristic, the assay composition can accurately determine the activity and/or concentration of anti-Factor $X_a$ and/or anti Factor $II_a$ compounds regardless of the presence of compounds such as aprotinin in a sample. Aprotinin can be administered to a subject to reduce the incidence of post-operative abnormal bleeding and blood transfusion due to activation of the fibrinolytic pathway. However, aprotinin in a subject can interfere with the results of some types of coagulation assays of samples from the subject. The present coagulation assay composition can be performed to accurately determine the activity and/or concentration of anti-Factor $X_a$ and/or anti Factor $II_a$ compounds such as heparin or hirudin, without having the accuracy or precision influenced by the presence of aprotinin in the sample.

1. General Combination Guidelines

In forming the coagulation assay composition provided herein, the components can be combined in relative amounts according to the desired clotting properties resultant from combining the components. In one embodiment, component ratios are determined according to the desired clotting time of the coagulation assay composition. For example, a Factor X compound composition can be combined with a Factor V compound composition and with blood or plasma, and the clotting time can be measured. One or more components can be increased or decreased in relative amount in achieving the desired coagulation properties. In one embodiment, the composition is formed such that Factor X compound is in excess (e.g., is not a rate limiting component). In another embodiment, the composition is formed such that Factor V compound is in excess (e.g., is not a rate limiting component). In another embodiment, the composition is formed such that Factor X compound and Factor V compound are in excess (e.g., are not rate limiting components). In another embodiment, the composition is formed such that multivalent cation, including divalent cation such as calcium or magnesium ion is in excess (e.g., is not a rate limiting component). In another embodiment, the composition is formed such that Factor X compound, Factor V compound and multivalent cation are in excess (e.g., are not rate limiting components). Typically, referral to excess of a component indicates that the amount of the component is sufficiently greater than the amount of at least one other factor involved in the coagulation cascade such that, for the amount of sample to be used, the rate of coagulation is not influenced by small changes in the amount of the component.

Coagulation properties typically include clotting time, where the clotting time for the resultant composition can be any amount of time suitable for the corresponding use that also provides sufficiently accurate results. For purposes of the present description, clotting time represents the time required for the coagulation assay composition to form a solid clot after addition of normal human blood (unless otherwise indicated) with the coagulation assay composition. Clotting times can be any of a wide range of times, from as short as about 1 second, to as long as multiple hours. Typically, clotting times will range from about 5 seconds to about 600 seconds or 5 seconds to 600 seconds, from about 5 seconds to about 300 seconds or 5 seconds to 300 seconds, from about 5 seconds to about 120 seconds or 5 seconds to 120 seconds, or from about 5 seconds to about 90 seconds or 5 seconds to 90 seconds. Exemplary clotting times can range from about 10 seconds to about 45 seconds or 10 seconds to 45 seconds.

Additional coagulation properties of the coagulation assay composition can include the ability for the clotting time and anticoagulant concentration to be linearly correlated. For example, when the anticoagulant is heparin, the clotting time resultant from combining the coagulation assay composition with normal human blood containing any of a range of heparin concentrations will form a straight line when clotting time is plotted against heparin concentration. Typically, the heparin concentrations of the range are biologically relevant heparin concentrations. The compositions provided herein can provide a linear correlation between clotting time and a variety of heparin concentrations, including 0 units/mL to about 20 units/mL, 0 units/mL to about 15 units/mL, 0 units/mL to about 12 units/mL, 0 units/mL to about 10 units/mL, 0 units/mL to about 7.5 units/mL, or 0 units/mL to about 5 units/mL. The compositions provided herein can provide a linear correlation between clotting time and a variety of heparin concentrations, including 0 units/mL to 20 units/mL, 0 units/mL to 15 units/mL, 0 units/mL to 12 units/mL, 0 units/mL to 10 units/mL, 0 units/mL to 7.5 units/mL, or 0 units/mL to 5 units/mL. In another example, when the anticoagulant is hirudin, the clotting time resultant from combining the coagulation assay composition with normal human plasma containing any of a range of hirudin concentrations will form a straight line when clotting time is plotted against hirudin concentration. Typically, the hirudin concentrations of the range are biologically relevant hirudin concentrations. The compositions provided herein can provide a linear correlation between clotting time and a variety of hirudin concentrations, including 0 µg/mL to about 20 µg/mL, 0 µg/mL to about 15 µg/mL, 0 µg/mL to about 12 µg/mL, 0 µg/mL to about 10 µg/mL, 0 µg/mL to about 7.5 µg/mL, or 0 µg/mL to about 5 µg/mL. The compositions provided herein can provide a linear correlation between clotting time and a variety of hirudin concentrations, including 0 µg/mL to 20 µg/mL, 0 µg/mL to 15 µg/mL, 0 µg/mL to 12 µg/mL, 0 µg/mL to 10 µg/mL, 0 µg/mL to 7.5 µg/mL, or 0 µg/mL to 5 µg/mL.

Any of a variety of known methods for determining the appropriate combination of components to achieve desired coagulation properties can be used. The following represents an exemplary procedure for arriving at an appropriate combination. One skilled in the art will recognize that many variations of the following procedure are possible, and are therefore contemplated herein. Factor X compound-containing solutions can be serially diluted. Factor V compound-containing solution can be combined with the various dilutions of Factor X compound solution and Normal Human Plasma (NHP). The Factor V compound solution also can be combined with the various dilutions of Factor X compound solution and Normal Human Plasma (NHP), where the NHP has added thereto an anticoagulant such as heparin. The Factor X compound dilution with the desired, or closest to desired, clotting properties can then be further, iteratively refined, or can be selected as the basis for combining the Factor X compound solution and the Factor V compound solution.

A Factor X compound dilution with desirable coagulation properties can be one that results in a clotting time of about 10-13 seconds or 10-13 seconds for normal plasma with no anticoagulant added, and a clotting time of about 35-50 seconds or 35-50 seconds for normal plasma with 3 units/mL heparin added thereto. If the Factor X compound dilution having a clotting time of about 35-50 seconds or 35-50 seconds for normal plasma with 3 units/mL heparin, has a clotting time less than about 10 seconds for normal plasma with no anticoagulant added, benzamidine-HCl can be added to the Factor V compound solution until the no anticoagulant added clotting time for that Factor X compound dilution is about 10-13 seconds or 10-13 seconds.

A Factor X compound dilution with desirable coagulation properties can be one that results in a clotting time of about 15-20 seconds or 15-20 seconds for normal plasma with no anticoagulant added, and a clotting time of about 40-55 seconds or 40-55 seconds for normal plasma with 3 units/mL heparin added thereto. If the Factor X compound dilution having a clotting time of about 40-55 seconds or 40-55 seconds for normal plasma with 3 units/mL heparin, has a clotting time less than about 15 seconds or 15 seconds for normal plasma with no anticoagulant added, benzamidine-HCl can be added to the Factor V compound solution until the no anticoagulant added clotting time for that Factor X compound dilution is about 15-20 seconds or 15-20 seconds.

Another example of a Factor X compound dilution with desirable coagulation properties can be one that results in a clotting time of about 13-17 seconds or 13-17 seconds for plasma with no anticoagulant added, and a clotting time less than about 100 seconds or 100 seconds for plasma with 7.5 units/mL heparin. If the Factor X compound dilution having a clotting time of less than about 100 seconds or 100 seconds for plasma with 7.5 units/mL heparin, has a clotting time less than about 13 seconds or 13 seconds for plasma with no anticoagulant added, Factor X compound solution can be further diluted, or the amount of lipid or detergent added to the Factor V compound solution can be reduced until a Factor X compound dilution is achieved with a no anticoagulant added clotting time about 13-17 seconds or 13-17 seconds and a clotting time of less than about 100 seconds or 100 seconds for plasma with 7.5 units/mL heparin.

Also contemplated herein, additional components can be added in varying amounts in arriving at the desired coagulation properties of the coagulation assay composition. Exemplary additional components include multivalent cation and lipid or detergent. For example, as increasing amounts of lipid or detergent are added, decreasing amounts of Factor X compound can be added, as is known in the art and exemplified in U.S. Pat. No. 4,851,336. Thus, in one example, the Factor-V solution can contain varying amounts of lipid or detergent, and these varying amounts can be compared to different dilutions of Factor X compound solution to arrive at a coagulation assay composition with the desired properties. One skilled in the art, based on the teachings herein and knowledge in the art will understand the relation between lipid or detergent and Factor X compounds, and will be able to determine suitable combinations of these components in achieving a desired coagulation assay composition.

Additional compounds can be present in a composition with one of the above compounds, or can, optionally be added in addition to the above compounds. Selection of components to add, and amounts of any added component, can be accomplished by the guidelines provided herein and known in the art, according to the desired coagulation properties of the resultant coagulation assay composition. Exemplary additional compounds include multivalent cation, lipid or detergent, reagent plasma, prothrombin complex, fibrinogen, antithrombin III, Factor II, anticoagulant, and combinations thereof.

Compositions also can be prepared that are directed toward coagulation assays for a subject to whom has been administered other anticoagulants, such as other anti-Factor $X_a$ or anti-Factor $II_a$ compounds, for example, hirudin. Such compounds can be prepared according to the guidelines provided above with respect to heparin, where the heparin is substituted with the other anticoagulant to be assayed. In one example, a hirudin-directed coagulation assay composition can be developed where the normal plasma or blood sample clotting time with no hirudin added is about 13-17 seconds or 13-17 seconds and the normal plasma or blood sample clotting time with about 7.5-10 µg/mL or 7.5-10 µg/mL added is less than about 100 seconds or 100 seconds. In another example, a hirudin-directed coagulation assay composition can be developed where the normal plasma or blood sample clotting time with no hirudin added is about 10-13 seconds or 10-13 seconds and the normal plasma or blood sample clotting time with about 3-5 μg/mL added is about 35-50 seconds or 35-50 seconds. In another example, a hirudin-directed coagulation assay composition can be developed where the normal plasma or blood sample clotting time with no hirudin added is about 15-20 seconds or 15-20 seconds and the normal plasma or blood sample clotting time with about 3-5 μg/mL added is about 40-55 seconds or 40-55 seconds.

2. Exemplary Compositions

By way of example, and not by limitation, the following exemplary compositions are provided. Variations according to the guidance provided herein and the knowledge of the art will be apparent to those skilled in the art. A diagram demonstrating exemplary preparations for the two exemplary compositions below, is provided in FIGS. 2, 3 and 4.

In one embodiment, a composition can contain components from two solutions, the first solution containing Factor $X_a$, and the second solution containing Factor V. The Factor $X_a$-containing solution can also contain buffer components such as Tris maleate, at pH 7.5, NaCl, BSA, PEG and lactose. In another example, the Factor $X_a$-containing solution can also contain buffer components such as Tris maleate, at pH 7.5, NaCl, glycine, BSA, PEG and lactose. The Factor $X_a$-containing solution can also contain a multivalent cation, such as calcium chloride. The amount of each of these components in the Factor $X_a$-containing solution is provided herein elsewhere. The Factor V-containing solution can contain a plasma fraction containing Factor V, where this plasma fraction can optionally be characterized as being substantially free of Factors II, VII, IX and X. The Factor V-containing solution can also contain buffer components, such as Tris maleate, at pH 7.5, NaCl, BSA, PEG and lactose. In another example, the Factor V-containing solution can also contain buffer components, such as Tris maleate, at pH 7.5, NaCl, BSA and PEG The Factor V-containing solution can also contain fibrinogen, such as mammalian fibrinogen, including bovine fibrinogen. The Factor V-containing solution can also contain lipid or detergent, such as rabbit brain cephalin. The Factor V-containing solution can also contain benzamidine HCl. The amount of each of these components in the Factor V-containing solution is provided herein elsewhere.

In another embodiment, a composition can contain components from two solutions, the first solution containing Factor $X_a$, and the second solution containing Factor V. The Factor $X_a$-containing solution can also contain buffer components such as Tris maleate, at pH 7.5, NaCl, BSA, PEG and lactose. The Factor $X_a$-containing solution can also contain a multivalent cation, such as calcium chloride. The Factor V-containing solution can contain a plasma fraction containing Factor V, where this plasma fraction can optionally be characterized as being substantially free of Factors II, VII, IX and X. The Factor V-containing solution can also contain buffer components, such as Tris maleate, at pH 7.5, NaCl, BSA, PEG and lactose. The Factor V-containing plasma fraction can also contain plasma, such as mammalian plasma, including normal human plasma or heparinized normal human plasma. The Factor V-containing plasma fraction can also contain prothrombin complex. The Factor V-containing plasma fraction can also contain an anticoagulant, such as heparin. The Factor V-containing solution can also contain lipid or detergent, such as rabbit brain cephalin. The Factor V-containing solution can also contain antithrombin III.

IV. Preparation of the Compositions

A. General Procedure Guidelines

The coagulation assay composition can be prepared by a process that includes adding two or more components of the composition under conditions in which the components do not react, and after adding, maintaining the composition under one or more different conditions under which the components do not react, until the time of use. In one embodiment, not all components of the composition can be present in an aqueous solution simultaneously without some reaction occurring. Accordingly, methods provided herein accomplish the addition of two or more components of the composition under conditions in which the components do not react by adding the components together under conditions in which not all components are substantially present in aqueous solution simultaneously. After such adding step, the composition is maintained under conditions in which not all components are substantially present in aqueous solution simultaneously, until the time of conducting the coagulation assay. Typically the methods provided herein include a method in which a Factor X compound-containing solution and a Factor V compound-containing solution are not both substantially present in aqueous solution simultaneously.

In another embodiment, coagulation assay composition can be prepared by a process that includes adding two or more components of the composition under conditions in which the components are substantially not admixed. For example, two aqueous solutions can be added to a vessel, where the first solution can be placed in a location or in a phase (e.g., solid phase) such that the first solution is not admixed with the second solution when the second solution is added to the vessel. In another example, two solids can be added to a vessel, and the conditions can be maintained such that the solids do not admix; such conditions include conditions that prevent the solids from substantially dissolving into a liquid or converting into liquid phase by, e.g., maintaining a cold temperature or an environment free of liquid or gaseous solvent material. In one such embodiment, a first and second component of the composition are combined such that the first and second compositions are not in fluid mixture with one another. In another such embodiment, a first and second component of the composition are combined such that the first and second compositions are not in a fluid composition with one another. Typically the methods provided herein include a method in which a Factor X compound-containing solution and a Factor V compound-containing solution are not both substantially present in aqueous solution simultaneously.

The multiple components so combined can be maintained in a form in which they do not react, are not substantially simultaneously present in liquid aqueous solution, are not substantially admixed, or are not substantially in fluid admixture, until performance of a coagulation assay. Maintaining the multiple components in such a form can be accomplished by maintaining constant or similar conditions to the conditions under which the components were combined, or can be accomplished by modifying the conditions to different conditions under which the components do not react, are not substantially simultaneously present in liquid aqueous solution, are not substantially admixed, or are not substantially in fluid admixture, until performance of a coagulation assay. Exemplary modification of conditions includes conditions in which any $H_2O$ present in the combined components is removed from the components without substantially transitioning to liquid form; such as by sublimation via, e.g., lyophilization.

In one method for accomplishing the adding steps in forming the coagulation assay compositions provided herein, two or more aqueous components are combined. For example, an aqueous Factor X compound-containing solution, which can also contain one or more additional components such as a divalent cation, can be combined with an aqueous Factor V compound-containing solution, which can contain one or more additional components such as fibrinogen, prothrombin complex, anticoagulant, lipid or detergent, or plasma. In such a method, the two components (the Factor X compound-containing solution and the Factor V compound-containing solution) are not both in aqueous liquid form when combined. For example, a first aqueous component can be present in a vessel in frozen, form. When the second component is added to the first component, the second component does not substantially cause the first component to transition to aqueous liquid form. This can be accomplished by bringing the frozen first component to a temperature of about −10° C. or less, about −20° C. or less, about −40° C. or less, about −60° C. or less, about −80° C. or less, or about −100° C. or less, or −10° C. or less, −20° C. or less, −40° C. or less, −60° C. or less, −80° C. or less, or −100° C. or less. The second component can be added to the frozen first component under conditions in which the second component freezes at a rate fast enough to not substantially cause the first component to transition to aqueous liquid form. Temperatures at which the second component freezes at a rate fast enough to not substantially cause the first component to transition to aqueous liquid form include about −10° C. or less, about −20° C. or less, about −40° C. or less, about −60° C. or less, about −80° C. or less, or about −100° C. or less, or −10° C. or less, −20° C. or less, −40° C. or less, −60° C. or less, −80° C. or less, or −100° C. or less. Typically, when three or more components are added, the additional component(s) are also added and frozen according to the same guidelines as the freezing of the second component.

In some embodiments, all of the two or more components are frozen on a short time scale. While not intending to be limited by the following, shorter time frames for freezing are considered to prevent aqueous solutions from transitioning to liquid form, and also to be conducive to maintaining biomolecules in active, native form. Accordingly, in some embodiments, freezing each of two or more components of the coagulation assay composition on a short time scale can produce a composition in which all components, while in frozen form, retain most, substantially all, or all activity relative to pre-frozen form, without having reacted with each other. Typically, freezing on short time scales can be accomplished by contacting small volumes of liquid with a low temperature, as is known in the art. Exemplary volumes that can be used include about 1 mL or less or 1 mL or less, typically about 100 µL or 100 µL. Exemplary temperatures that can be used include −10° C. or less, about −20° C. or less, about −40° C. or less, about −60° C. or less, about −80° C. or less, or about −100° C. or less, or −10° C. or less, −20° C. or less, −40° C. or less, −60° C. or less, −80° C. or less, or −100° C. or less. Any of a variety of quick freezing methods known in the art can be used to quickly freeze the component-containing liquids provided herein.

In one example of the above description, 100 µL of a first solution containing Factor V compound and cephalin is contacted with a glass vessel, where the contacting surface of the glass vessel is about −90° C. or −90° C. Before adding the second solution, the frozen first solution is maintained in contact with the glass at −90° C. until the frozen first solution reaches about −90° C. or −90° C. Next, 100 µL of a second solution, which contains Factor $X_a$ and calcium chloride, is contacted with the glass vessel containing the frozen first solution, and at a temperature of about −90° C. or −90° C.

An exemplary apparatus for low temperature combination of components of the composition includes a cooling block, for example, an aluminum block cooled to the desired temperature. Such a cooling block can be placed into the desired temperature for sufficient time to adopt that temperature (e.g., overnight in a freezer or on dry ice) or can have circulated within the block a fluid that is at or below the desired temperature (e.g., liquid nitrogen, gaseous nitrogen, ethanol from an ethanol/dry ice bath). Any of a variety of methods known in the art for attaining and maintaining a desired temperature can be used for combination of components of the composition according to the teachings provided herein.

When the first and second components are combined in a vessel, the vessel can be any suitable vessel for containing the components. In one embodiment, the vessel also is suitable for subsequently performing coagulation assay methods. In another embodiment, the vessel can contain a single compartment. In another embodiment, the vessel can contain multiple compartments. In some embodiments, the vessel can be a sterile vessel.

Further to the above example, after both solutions are frozen and sufficiently cooled, the vessel is transferred to a lyophilizer without permitting the solutions to return to liquid state. Lyophilization can be performed at normal lyophilization conditions until substantially all $H_2O$ is removed from the vessel, for example, for about 8 hours or 8 hours. The vessel can then be sealed under vacuum with a vapor-impermeable seal, and maintained at room temperature, or cooler temperatures.

In some instances, the vessels containing the lyophilized compositions will contain discrete masses, where substantially all of the components of each discrete mass are components from only one of the liquids that were flash-frozen. For example, a vessel containing lyophilized composition can contain a first discrete mass containing substantially only components from the Factor V compound-containing solution, and a second discrete mass containing substantially only components from the Factor X compound-containing solution.

V. Measuring Anticoagulants

Also provided herein are methods of determining the amount of anticoagulant in a sample. Typically the amount compound(s) having anti-Factor $X_a$ and/or anti Factor $II_a$ activity can be determined using the methods provided herein. In one embodiment, the coagulation assay composition provided herein can be used in a one-step procedure for performing the assay. Any of a variety of general procedures for assaying coagulation known in the art can be used in the coagulation assay methods provided herein. The following guidelines are intended to exemplify assay procedures; other assay procedures known in the art can also be used in performing the assay.

A. General Protocol Guidelines

The coagulation assay composition provided herein can be used in methods that determine the propensity of a sample from a subject to coagulate. For example, the composition can be used to determine the influence of compounds that inhibit Factor $X_a$ or Factor $II_a$ in a subject's blood or plasma. In one example, the composition can be used to determine the influence of heparin on coagulation of a subject's blood or plasma. In another example, the composition can be used to determine the influence of hirudin on coagulation of a subject's blood or plasma. Generally, the method is performed by adding a sample, such as blood or plasma, to the coagulation assay composition, mixing the sample and the composition, and monitoring the time between adding the sample to the composition and a reaction endpoint such as clot formation. Each step, such as adding, mixing and monitoring, can be performed by any of a variety of methods known in the art. For example, the assay can be performed by any of a variety of methods known in the art for determining the propensity of a sample from a subject to coagulate. Typically, the time monitored begins upon adding the sample to the coagulation assay composition, and ends at an endpoint such as clot formation. The results of the assay can be used to determine the clotting time of the sample, the clotting time of the sample relative to the clotting time of a reference, or the amount of anticoagulant in the sample, as determined by comparison to a calibration or reference curve.

1. Sample Treatment

A sample used in the coagulation assay methods provided herein can be any biological fluid from a subject that contains one or more compounds that influence blood coagulation. Generally, the sample is in liquid form when added to the coagulation assay composition. Exemplary samples include, but are not limited to blood, plasma, serum, interstitial fluid, and lymph. Typical samples are blood and plasma.

A sample collected from a subject can be tested immediately after collection, or can be stored and later tested. In one example, a blood sample can be collected by clean venipuncture in a plastic tube containing 3.8% sodium citrate, and used immediately after collection, or stored, or treated in one or more steps, such as centrifugation where the plasma is collected an assayed. Typically, when a sample is stored for more than about 2 hours, the sample can be treated in any manner known in the art for storing such a sample, according to the sample type and time period over which the sample is to be stored. Storage conditions can include temperatures such as 4° C. or below 0° C. For example, plasma can be stored at about 4° C. for about 24 hours, or longer, as is known in the art. Storage conditions can also include addition of one or more compounds to the sample that are known in the art for preserving samples such as blood or plasma samples, for extended time periods. As an alternative to, or in combination with addition of one or more compounds, a sample can have removed therefrom, one or more compounds; for example, a blood sample can have removed therefrom its cellular components, leaving only the plasma portion of the blood. Appropriate storage and treatment methods can be selected according to the type of sample and the length of storage time, as is known in the art. In some embodiments, a sample stored at room temperature or below, can be warmed to a temperature ranging from about room temperature to about 37° C., or room temperature to 37° C., before performing the assay. A warmed sample can be incubated at the selected temperature for about 1 to about 10 minutes or 1 to 10 minutes. Similarly, the vessel in which the assay is to be performed (e.g., the vessel containing the coagulation assay composition) can be warmed to the selected temperature.

A sample can also have added thereto one or more compounds or compositions, prior to performing the coagulation assay. For example, a sample can have added thereto coagulation suppressing compounds or solutions, as known in the art, for example, a sodium citrate solution, a sodium or potassium oxalate solution, or EDTA. A typical composition added to a sample is a 3.8% sodium citrate solution.

2. Adding Sample and Coagulation Assay Composition

The coagulation assay can be initiated by adding the sample to a vessel containing the coagulation assay composition. As an alternative, the coagulation assay composition can be added to a vessel containing the sample. Upon adding the sample and coagulation assay composition, the sample and coagulation assay composition disperse and become admixed together. Typically, the sample is a liquid sample and the coagulation assay composition is a solid and, upon adding the liquid sample and coagulation assay composition, the components of the coagulation assay composition disperse into the liquid sample such that the components of the sample can react with the components of the coagulation assay composition. In assays that measure time periods, the addition of the sample and coagulation assay composition typically represents the starting point of the assay. Thus, upon adding the sample and coagulation assay composition, a time measuring device, such as a stopwatch or electronic timer, including a timer integral to a device such as a coagulometer, can be started. Any of a variety of methods for monitoring coagulation assay time periods are known in the art, and can be used in the coagulation assay methods provided herein.

Upon adding the sample and coagulation assay composition, if desired, the sample and coagulation assay composition can be mixed by any of a variety of methods known in the art. For example, the sample and coagulation assay composition can be mixed by sealing the vessel and inverting the vessel once or a plurality of times, or the sample and coagulation assay composition can be mixed using a vortex mixer. The mixing can be performed until most or substantially all components are dispersed and/or dissolved. For example, the sample can coagulation assay composition can be mixed for a time period ranging from about 3 seconds to about 5 seconds or 3 seconds to 5 seconds. Typically, the sample can coagulation assay composition can be mixed for about 5 seconds or 5 seconds.

The amount of sample to be added to the coagulation assay composition can be any of a wide range of volumes, according to the assay design (e.g., amount of coagulation assay composition to be used, device used in monitoring coagulation, convenience of sample collection and treatment, desired accuracy of the assay, desired time duration of the assay), as is known in the art. For example, an assay can be designed to accommodate a sample volume of about 5 mL to about 0.1 mL, typically about 0.5 mL. In another example, an assay can be designed to accommodate a sample volume of 5 mL to 0.1 mL, typically 0.5 mL.

3. Monitoring the Assay

After adding and/or mixing the sample and coagulation assay composition, the assay mixture can be monitored for an endpoint, such as clot formation. Typically, the endpoint monitoring is performed while observing the amount of time after the start of the assay for the endpoint to be attained. In such instances, upon arriving at the endpoint, the time period between the point of adding the sample and coagulation assay composition to the endpoint can represent the clotting time for the coagulation assay.

The endpoint to be monitored can be defined according to the assay design, as is known in the art. Typically, the endpoint will be marked by the formation of a solid clot. Any of a variety of methods for monitoring an endpoint of a coagulation assay, such as solid clot formation, are known in the art, including, but not limited to, visual monitoring, fibrometer monitoring (BBL Fibrosystems, Franklin Lakes, N.J.), electrochemical monitoring (using e.g., an i-STAT analyzer, i-STAT Corp., East Windsor, N.J.), magnetic particle mobility monitoring (using e.g., a Behnk Thrombostat Coagulometer, Behnk Elektronic GmbH & Co, Norderstedt, Germany), magnetic particle stationary position monitoring (using, e.g., a KC1A Coagulometer, Amelung GMBH, Lemgo, Germany), viscoelasticity monitoring (Sonoclot Analyzer, Sienco, Inc., Morrison, Colo.); electromechanical meter (Hemo Tec or Hepcon HMS Plus or ACT Plus, Medtronic Inc., Minneapolis, Minn.)). For example, visual monitoring can be performed by tilting or inverting the vessel containing the sample and coagulation assay composition in order to visually observe the formation of a clot, as known in the art. In another example, the assay can be conducted in a vessel containing a magnetically responsive particle, such as a steel ball, the movement of which can be driven and monitored by a device having a magnetic field; when the motion of the particle falls below a defined amount, this can indicate that the endpoint has been reached.

4. Results

The results typically are determined according to the time period between the point of adding the sample and coagulation assay composition, and the endpoint. Results can be reported in terms of the time for the assay (e.g., as the amount of time between adding the sample and the coagulation assay composition and clot formation), or in relative terms of a ratio between sample assay time and the assay time for a reference such as normal blood or normal plasma. Results can also be reported in terms of units of anticoagulant per unit volume, such as units/mL of Factor $X_a$ inhibitor or units/mL of Factor $II_a$ inhibitor. For example, results can be reported as units/mL of heparin or μg/mL of hirudin; this can be accomplished by comparing the assay time to a reference curve of anticoagulant factor concentration plotted vs. assay time.

In one embodiment, the clotting time and anticoagulant concentration to be measured are linearly correlated. For example, the methods provided herein can result in clotting times for normal plasma or blood, which have added thereto any of a range of anticoagulant concentrations, that form a straight line when clotting time is plotted against anticoagulant concentration. The methods provided herein can yield a linear correlation between clotting time and anticoagulant for a variety of anticoagulants and for a variety of anticoagulant concentrations. For example, when the anticoagulant is heparin, the methods provided herein can result in a linear relationship between clotting time and heparin concentration for ranges such as 0 units/mL to about 20 units/mL, 0 units/mL to about 15 units/mL, 0 units/mL to about 12 units/mL, 0 units/mL to about 10 units/mL, 0 units/mL to about 7.5 units/mL, or 0 units/mL to about 5 units/mL. In another example, when the anticoagulant is hirudin, the methods provided herein can result in a linear relationship between clotting time and hirudin concentration for ranges such as 0 μg/mL to about 20 μg/mL, 0 μg/mL to about 15 μg/mL, 0 μg/mL to about 12 μg/mL, 0 μg/mL to about 10 μg/mL, 0 μg/mL to about 7.5 μg/mL, or 0 μg/mL to about 5 μg/mL. In another example, when the anticoagulant is heparin, the methods provided herein can result in a linear relationship between clotting time and heparin concentration for ranges such as 0 units/mL to 20 units/mL, 0 units/mL to 15 units/mL, 0 units/mL to 12 units/mL, 0 units/mL to 10 units/mL, 0 units/mL to 7.5 units/mL, or 0 units/mL to 5 units/mL. In another example, when the anticoagulant is hirudin, the methods provided herein can result in a linear relationship between clotting time and hirudin concentration for ranges such as 0 μg/mL to 20 μg/mL, 0 μg/mL to 15 μg/mL, 0 μg/mL to 12 μg/mL, 0 μg/mL to 10 μg/mL, 0 μg/mL to 7.5 μg/mL, or 0 μg/mL to 5 μg/mL. When said linear relationship is determined, the number of different heparin or hirudin concentrations can be 2 or more, 3 or more, 4 or more, 5 or more or 6 or more, where typically most or all of the different heparin or hirudin concentrations differ in concentration by the same incremental amount (e.g., 0 units/mL, 5 units/mL, 10 units/mL, 15 units/mL and 20 units/mL).

B. Exemplary Protocol

By way of example, and not by limitation, the following assay procedures are provided. Variations according to the guidance provided herein and the knowledge in the art will be apparent to those skilled in the art.

In a first example, fresh blood from a subject can be mixed with a 3.8% sodium citrate solution in volume ratios 9:1 (blood:sodium citrate solution), to a total volume of 2 mL. A 0.5 mL aliquot of the blood sample is then added to a siliconized glass vessel containing the coagulation assay composition, and the solution is inverted by hand for 3-5 seconds, or until fully mixed. Time monitoring of the reaction begins upon addition of the sample to the composition. After mixing, the vessel is repeatedly inverted and visually inspected for clot formation. Clot formation is determined by formation of a solid clot in the vessel. Time monitoring of the reaction ends upon clot formation.

In a second example, fresh blood from a subject can be mixed with a 3.8% sodium citrate solution in volume ratios 9:1 (blood:sodium citrate solution), to a total volume of 2 mL. A 0.5 mL aliquot of the blood sample is then added to a siliconized glass vessel containing the coagulation assay composition and a 2 mm steel ball, and the solution is mixed for 3-5 seconds using a vortex mixer. Time monitoring of the reaction begins upon addition of the sample to the composition. Immediately after mixing, the vessel is placed onto a Behnk Thrombostat coagulometer configured to monitor the motion of the 2 mm steel ball in determining the coagulation assay endpoint. The coagulometer monitors the motion of the steel ball, and monitors the time elapsed until an endpoint, such as clot formation, is reached. Clot formation is detected by impairment of movement of the steel ball. Time monitoring of the reaction ends upon clot formation.

The results of the assay can be reported as the amount of time between introduction of the sample to the composition and clot formation for the sample, or as a ratio of the amount of time between introduction of the sample to the composition and clot formation for the sample relative to the amount of time between introduction of the sample to the reagent and clot formation for a standard or reference, or can be units of anticoagulant/mL as determined by comparing the clotting time to a reference curve.

C. Enhanced Clotting Inhibition

A subject sample can have added thereto an anticoagulant such as heparin or hirudin, and then be subjected to the clotting assay, as provided herein. Typically, several samples from a subject are used or several aliquots of a sample from a subject are used, where different samples can contain different amounts of the anticoagulant, to thereby construct a curve of the clotting response as influenced by added anticoagulant. In this assay, a sample from a subject is mixed with a known amount of anticoagulant such as heparin or hirudin, and also can be mixed with a coagulation inhibiting solution such as sodium citrate. The anticoagulant/sample mixture can then be added to the coagulation assay composition, and the clotting assay performed according to the general parameters provided herein.

The anticoagulant that can be used in performing such test can be any anticoagulant known in the art to inhibit Factor $X_a$ or Factor $II_a$. Exemplary anticoagulants that can be used include heparin and hirudin. Results from the test can be plotted on a curve to determine the response of the subject to the anticoagulant. As described herein, the curve can be a straight line over a range of anticoaglant concentrations.

D. Standard Curve

Similar to the method of enhancing clotting inhibition of a subject sample, a standard sample, such as normal human plasma can have added thereto an anticoagulant such as heparin or hirudin, and then be subjected to the clotting assay, as provided herein. Typically, several standard samples or several aliquots of a standard sample are used, where different samples can contain different amounts of the anticoagulant, to thereby construct a standard curve of the clotting response as influenced by added anticoagulant. In this assay, a standard sample is mixed with a known amount of anticoagulant such as heparin or hirudin, and also can be mixed with a coagulation inhibiting solution such as sodium citrate. The anticoagulant/sample mixture can then be added to the coagulation assay composition, and the clotting assay performed according to the general parameters provided herein.

As described herein, the curve can be a straight line over a range of anticoagulant concentrations. Typically, when the curve is a straight line, the range of anticoagulant concentrations includes concentrations clinically relevant for the application. For example, the range can be one relevant for screening subjects for their blood's propensity to clot; one relevant for pre-operative determination of the propensity of a subject's blood to clot; one relevant for determination of the propensity of a subject's blood to clot during an operation; one relevant for post-operative determination of the propensity of a subject's blood to clot. Exemplary operations for such use are open-heart and/or coronary bypass operations. The range of concentration for which the anticoagulant concentration and clotting time are linear can be determined in the preparation of the coagulation assay composition, as provided herein.

E. Properties of Methods

In one embodiment, the coagulation assay methods provided herein can be performed to accurately determine anticoagulant concentrations for a subject whose blood has undergone hemodilution. Subjects undergoing surgery such as coronary bypass surgery can have their blood diluted by a large percent, such as about 25-60% or 25-60%. To such subjects, anticoagulants such as heparin are routinely administered. However, dilution of the blood can result in uncertainties as to the amount of anticoagulant present in the subject's diluted blood when tested using methods other than those provided herein (e.g., ACT test). The methods provided herein can be used to accurately determine the concentration of such anticoagulants. Methods are performed substantially as provided above, and the clotting time can be used to determine the concentration of anticoagulant in the sample. By virtue of the linear correlation between clotting time and anticoagulant concentration at clinically relevant concentrations (e.g., heparin concentrations ranging from 0 units/mL to about 7.5 units/mL), the concentration of anticoagulant can be accurately measured even after having undergone hemodilution and administration of exogenous anticoagulant. Thus, the present coagulation assay methods can be performed for a subject that has undergone hemodilution, to determine the activity and/or concentration of anti-Factor $X_a$ and/or anti Factor $II_a$ compounds such as heparin or hirudin without the accuracy or precision of the assay being influenced by hemodilution.

In another embodiment, the coagulation assay methods can be performed to accurately determine the activity and/or concentration of anti-Factor $X_a$ and/or anti Factor $II_a$ compounds regardless of the presence of compounds such as aprotinin or abciximab in a sample. Aprotinin can be administered to a subject to reduce the incidence of post-operative abnormal bleeding and blood transfusion due to activation of the fibrinolytic pathway. However, aprotinin in a subject can interfere with the results of some coagulation assay methods of samples from the subject. The present coagulation assay methods can be performed to determine the activity and/or concentration of anti-Factor $X_a$ and/or anti Factor $II_a$ compounds such as heparin or hirudin, without having the accuracy or precision influenced by the presence of aprotinin in the sample.

In another embodiment, the coagulation methods can be performed to accurately determine the activity and/or concentration of anti-Factor $X_a$ and/or anti-Factor $II_a$ compounds regardless of the temperature of the sample. In some instances, a subject can be tested for clotting activity of the subject's blood while the blood is kept at temperatures far below normal body temperature (e.g., temperatures ranging from about 27° C. to about 22° C. or 27° C. to 22° C.). Lower temperatures of the sample can slow the assay time for some assay methods. However, the present assay methods are not substantially affected by lower temperatures of the sample. Further, standard curves of normal plasma or blood can be established at any of a variety of temperatures such that quantitative results can be obtained notwithstanding the lower temperatures. Thus, the present coagulation assay methods can be performed to determine the activity and/or concentration of anti-Factor $X_a$ and/or anti Factor $II_a$ compounds such as heparin or hirudin, without having the accuracy or precision influenced by lower sample temperatures.

Figure 2A:
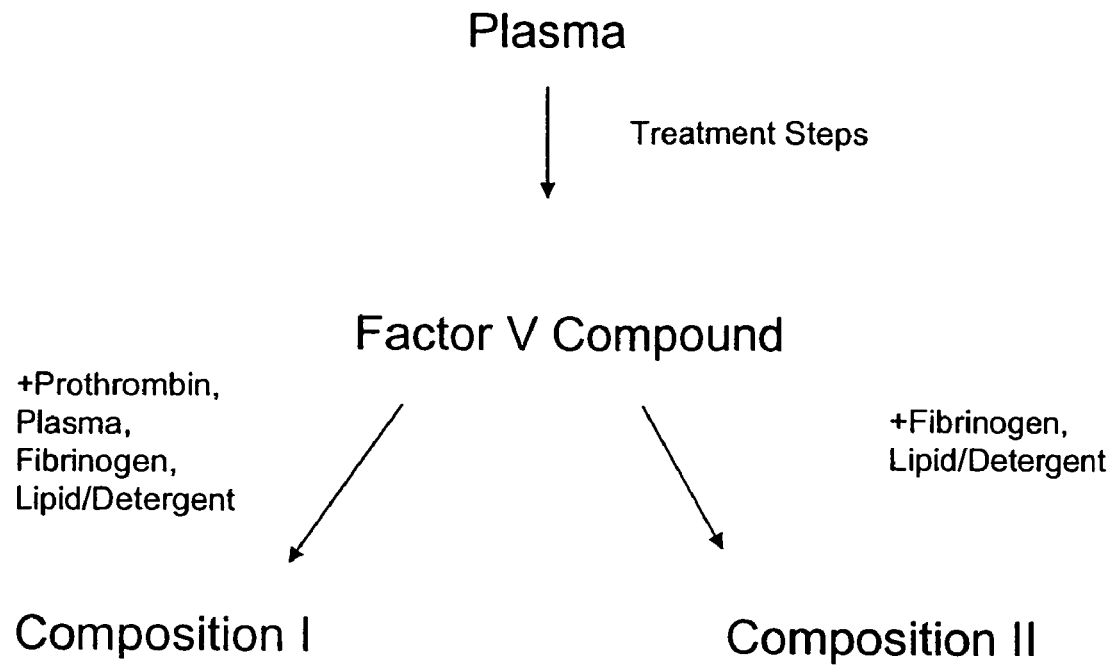
FIG. 2A demonstrates formation of a Factor V compound-containing solution.
Figure 2B:
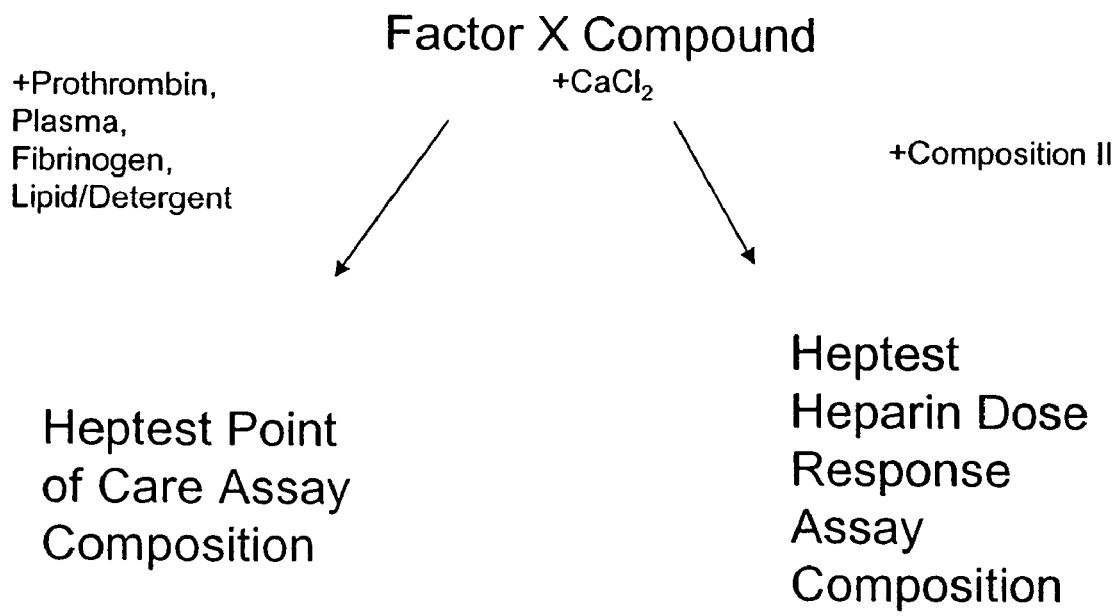
FIG. 2B demonstrates combining Factor X compound-containing solution with Factor V compound-containing solution.
Figure 3:
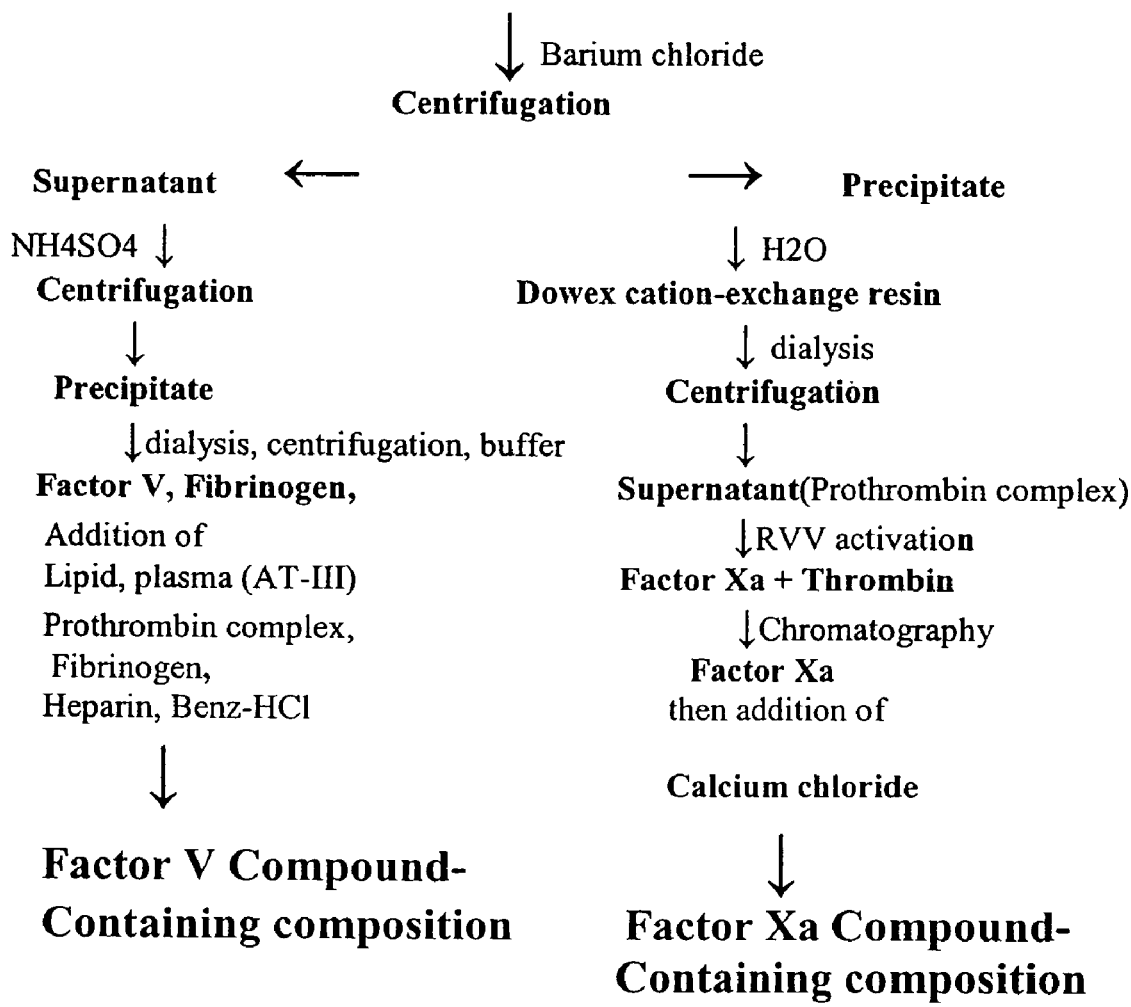
FIG. 3 is a diagram depicting exemplary components of coagulation assay compositions for point-of-care use, and steps for forming such compositions in accordance with the methods provided herein.

In another embodiment, the coagulation methods can be performed to accurately determine the activity and/or concentration of anti-Factor $X_a$ and/or anti-Factor $II_a$ compounds in a time frame and with sufficient simplicity so as to be used at the point of care. In one example, the coagulation methods provided herein can be performed while a subject is physically present at clinic or other care-giving or diagnostic facility. In another example, the coagulation methods provided herein can be performed during the course of a surgical procedure, such as during open heart surgery. In another example, the coagulation methods provided herein can be performed immediately prior to surgery. In another example, the coagulation methods provided herein can be performed immediately subsequent to surgery. Such methods further can be performed on a multiplicity of occasions, as the occasion requires. For example, the blood of a subject undergoing a surgical procedure can be tested a multiplicity of occasions, such as, but not limited to, on two or more occasions during the course of the surgery, one assay every designated time period (e.g., once every 30 minutes or every hour), prior to surgery and during surgery, during surgery and subsequent to surgery, on multiple occasions prior to surgery, on multiple occasions subsequent to surgery, and combinations thereof. In one embodiment, the composition formulated for point of care coagulation assay methods is a composition in which the Factor V compound is present in a plasma fraction which has had added thereto prothrombin, plasma, fibrinogen and lipid or detergent, and the Factor X compound can have added thereto a multivalent cation salt. An example of a composition that can be used for point of care applications is provided in FIGS. 2A, 2B, 3 and 4. In FIG. 2A, Composition I can be combined with a Factor X compound-containing composition to form a Point of Care Assay Composition. In FIG. 3, a flow chart of an exemplary process for preparing Factor V compound-containing composition and Factor X compound-containing composition for preparation of a Point-of-Care coagulation assay composition are presented.

Figure 4:
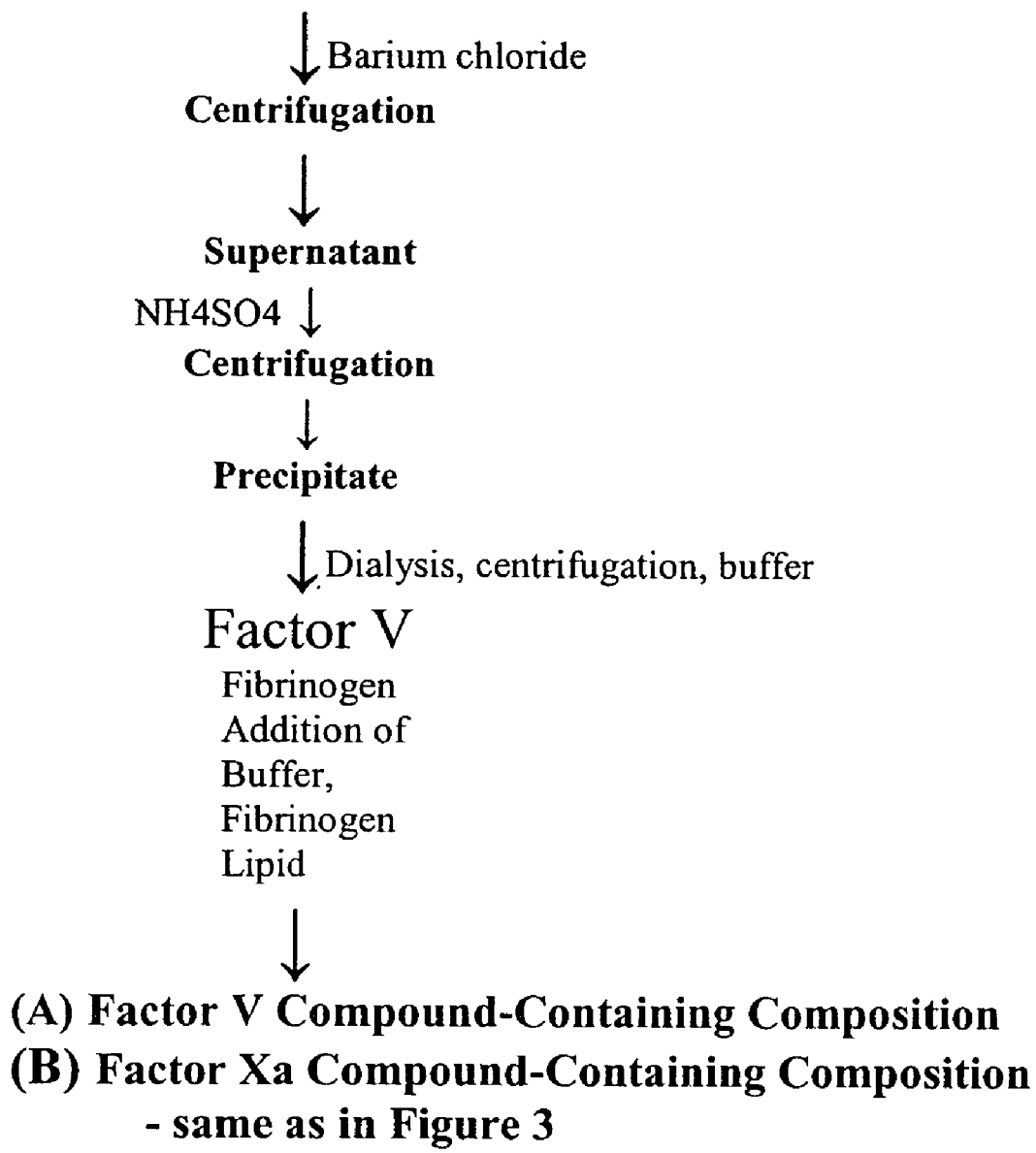
FIG. 4 is a diagram depicting exemplary components of coagulation assay compositions for dose-response use, and steps for forming such compositions in accordance with the methods provided herein.

In another embodiment, the coagulation methods can be performed to accurately determine the activity in the blood of a subject of anti-Factor $X_a$ and/or anti-Factor $II_a$ compounds at different anti-Factor $X_a$ and/or anti-Factor $II_a$ compound concentrations. A sample from a subject can have added thereto one or more different concentrations of anti-Factor $X_a$ and/or anti-Factor $II_a$ compound (e.g., heparin or hirudin), a coagulation method can be performed for each concentration, and the influence of the anti-Factor $X_a$ and/or anti-Factor $II_a$ compound on the clotting time of the sample can be determined. In another embodiment of such methods, the subject can have added thereto one or more different concentrations of anti-Factor $X_a$ and/or anti-Factor $II_a$ compound (e.g., heparin or hirudin), a coagulation method can be performed for each concentration, and the influence of the anti-Factor $X_a$ and/or anti-Factor $II_a$ compound on the clotting time of the blood of the subject can be determined. An exemplary composition that can be formulated for a coagulation assay methods that determine clotting time at different concentrations of anti-Factor $X_a$ and/or anti-Factor $II_a$ compound is a composition in which the Factor V compound is present in a plasma fraction which has had added thereto fibrinogen and lipid or detergent, and the Factor X compound can have added thereto a multivalent cation salt. An example of a composition that can be used for point of care applications is provided in FIGS. 2A and 2B, where Composition II of FIG. 2B can be combined with a Factor X compound-containing composition to form a Heparin Does Response Assay Composition. In FIG. 4, a flow chart of an exemplary process for preparing Factor V compound-containing composition and Factor X compound-containing composition for preparation of a Dose Response coagulation assay composition are presented. Such methods can be used, for example, to indicate that a subject may have an anti-thrombin III deficiency, an anti-heparin antibody, or other medication that might reduce the ability of heparin and/or hirudin to inhibit coagulation, when clotting times are shorter than expected. Such methods also can be used, for example, or to indicate that a subject may have anticoagulant drugs, when clotting times are longer than expected.

F. Variations of the Method

The methods provided herein can be used by adding a sample, such as a blood sample, to a vial containing a lyophilized coagulation assay composition provided herein. Also contemplated herein, the methods can include adding a sample to a first liquid containing Factor X compound and adding the sample/Factor X compound combination to a liquid or solid containing Factor V compound. Also contemplated herein, the methods can include adding a sample to a first liquid containing Factor V compound and adding the sample/Factor V compound combination to a liquid or solid containing Factor X compound. Also contemplated herein, the methods can include adding a sample to a first solid containing Factor X compound and adding the sample/ Factor X compound combination to a liquid or solid containing Factor V compound. Also contemplated herein, the methods can include adding a sample to a first solid containing Factor V compound and adding the sample/Factor V compound combination to a liquid or solid containing Factor X compound. In such methods, Factor V compound-containing composition and Factor X compound-containing composition typically are not mixed prior to contacting either the Factor V compound-containing composition or the Factor X compound-containing composition with sample. In such methods, Factor X compound can be present in excess relative to the amount of sample. Also in such methods, Factor V compound can be present in excess relative to the amount of sample. Also in such methods, multivalent cation salt can be present in excess relative to the amount of sample. In such methods, sample and Factor X compound-containing composition are typically not in contact with each other for more than about 2 seconds or 2 seconds, prior to contacting the sample/Factor X compound-containing solution with Factor V compound.

VI. Combinations and Kits

Also provided herein are combinations and kits, wherein the combinations and kits contain the coagulation assay composition provided herein, in combination with one or more additional constituents. Any of a variety of additional constituents can be provided in combination with the compositions provided herein; additional constituents can, for example, assist in performing a coagulation assay, assist in interpreting the results of a coagulation assay, or assist in constructing a reference for comparison with a coagulation assay.

In one embodiment, the coagulation assay composition is provided with one or more constituents that assist in performing the assay. For example, the composition can be provided with a vessel containing the composition. The vessel can be a vessel in which the composition is stored for time periods between preparation of the combinations and use of the combination. The vessel can be a vessel in which the coagulation assay is to be performed. The vessel also can be for both storage and performing the assay. Typically, a vessel in which the composition is stored will be sealed with a vapor-impermeable seal, or otherwise configured to prevent liquid or gaseous $H_2O$ from entering the vessel in which the composition is contained. Storage vessels can be constructed of any of a variety of substances known in the art for vapor impermeable storage of compositions, including, but not limited to glass. In some instances, when the vessel is the vessel in which the assay is to be performed, the portion of the vessel in contact with the composition and blood or blood sample, typically the inner surface of the vessel, can have a surface in which aqueous solutions in contact with the surface have a high surface tension. An example of such a high surface tension surface is siliconized glass. Another example of such a high surface tension surface is various plastics known in the art. In some embodiments, the high surface tension surface such as siliconized glass will be substantially homogenous; that is, the surface tension of the entire surface is substantially the same.

In another embodiment, the combination can include an object for monitoring coagulation of the sample. The object can be an object that, upon application of a magnetic field, can be moved by the magnetic field. Thus, objects can contain a substance sensitive to magnetic fields, such as iron based substances, including steel. The object can be configured such that, when the object is present in a solution that does not contain a clot, the object can move within the solution with relative ease, but when the object is present in a solution that does contain a clot, object movement is impaired to a large enough degree as to be measurable by a device that can monitor such movements. Any of a variety of shapes for the particle can be used, including but not limited to, spheres, cubes, or irregularly shaped particles, provided that the particle possesses the intended motile properties. An exemplary shape is a ball. In one example, a steel ball can be used that has a diameter of about 2 mm or 2 mm. The object, when present in a combination, can be provided within the same compartment as the coagulation assay composition (e.g., within the same vessel as the composition) or in a separate compartment, where the object can be added with the composition at the time of performing the coagulation assay.

In another embodiment, a combination can include a device for monitoring a coagulation assay endpoint, such as clot formation. Any of a variety of known devices for monitoring coagulation assays can be provided herein, including, but not limited to a fibrometer (BBL Fibrosystems, Franklin Lakes, N.J.), an electrochemical analyzer (e.g., the i-STAT analyzer from i-STAT Corp., East Windsor, N.J.), a magnetic particle mobility monitoring meter (e.g., the Behnk Thrombostat Coagulometer from Behnk Elektronic GmbH & Co, Norderstedt, Germany), magnetic particle stationary position monitoring (using, e.g., a KC1A Coagulometer, Amelung GMBH, Lemgo, Germany), viscoelasticity monitoring meter (e.g., the Sonoclot Analyzer from Sienco, Inc., Morrison, Colo.); electromechanical meter (Hemo Tec or Hepcon HMS Plus or ACT Plus, Medtronic Hemo Tec, Medtronic Inc., Minneapolis, Minn.). In one embodiment, a combination can include device for monitoring movement of the coagulation monitoring object within the sample. Such a device can be a device that can form a magnetic field and/or can monitor magnetic field influences of the coagulation monitoring object. Any of a variety of devices for monitoring movement of a magnetically influenceable object can be used, as known in the art. In one example, such a device can contain a flat horizontal surface upon which the sample can be placed, and below which is located device components that can form a magnetic field and/or can monitor magnetic field influences of the coagulation monitoring object. An exemplary device is the Behk Thrombostat coagulometer.

In another embodiment, a combination can include a blood collector and/or a blood sample container. The blood collector can be any of a variety of apparatuses known in the art for the collection of blood. As an integral or separate constituent, a combination can contain a blood sample container, which can be any object able to contain a liquid such as blood, typically a sterile object. A blood sample container can also contain a coagulation inhibitor, as are known in the art. An exemplary blood sample container can contain a 3.8% sodium citrate solution, where the volume of the sodium citrate solution can be about ⅒ or ⅒ the final volume after blood is added to the sodium citrate solution.

A kit can contain any of the combinations provided herein, and also optionally additional components such as instructions for use of the assay composition, information for interpreting the results that can include a reference curve or table (e.g., a curve in which reference amounts of heparin are plotted against clotting time), liquid dispensing apparatuses (e.g., pipettes), a device for mixing a vessel containing blood or a blood sample and the coagulation assay composition (e.g., a vortex mixer), a device for monitoring time elapsed during the coagulation assay (e.g., a stopwatch).

A kit also can contain additional chemical components separately packed from the coagulation assay composition. One additional chemical component can be, for example, an anticoagulant such as heparin or hirudin, which can be used for calibrating or standardizing multiple coagulation assay compositions, or can be used for addition into the sample or assay solution in determining the influence of exogenous anticoagulant on the subject's sample, or can be administered to a subject in monitoring the response of the subject to the anticoagulant, or can be administered to a subject therapeutically, if appropriate, after determining the results of the coagulation assay. Another additional chemical component can be, for example, plasma (e.g., Normal Human Plasma), which can have as its source one or more subjects, and can optionally contain added thereto, an anticoagulant such as heparin or hirudin.

The packaging material used in the kit can be one or more physical structures used to house the contents of the kit, and can be constructed by well known methods, typically to provide a contaminant-free environment. The packaging material can have a label that indicates the components of the kit. In addition, the packaging material contains instructions indicating how the materials within the kit are employed to perform a coagulation assay or to interpret the results of a coagulation assay. Instructions typically include a tangible expression describing the steps of performing the assay and/or at least one assay method parameter, such as the amount of sample to add with the coagulation assay composition, methods of mixing, and methods of monitoring coagulation. The kit can include one or more containers capable of holding within fixed limits the coagulation assay composition, or buffer solution, or other composition used in the coagulation assay methods. For example, a kit can include a glass vial used to contain the coagulation assay composition.

The following examples are included for illustrative purposes only and are not intended to limit the scope of the invention.

EXAMPLES

Example 1

Nine liters of bovine blood was anticoagulated with one liter of 3.8% sodium citrate solution and then centrifuged at 2500×g to remove blood cells. To one liter of the resulting plasma was added 7.35 g of trisodium citrate, which was stirred to dissolve the citrate, followed by the addition of 20.825 g of solid barium chloride at room temperature over a period of about 90 minutes. The heavy precipitate which formed was removed by centrifugation of the plasma mixture at 3000×g for about 20 minutes, leaving a clear plasma supernatant. 270 g of solid ammonium sulfate was added to the clear plasma supernatant at room temperature and allowed to set for 90 minutes and then centrifuged at 4000×g for 15 minutes, and a precipitated protein fraction obtained. The recovered precipitated protein fraction was dissolved in 350 ml of distilled water and then dialysed against a 0.9 NaCl solution or tap water until all ammonium ions had been removed. The dialysed plasma fraction was then clarified by centrifugation at 3000×g for 15 minutes at room temperature and then buffered to a pH of 7.5 by mixing nine volumes of the dialysed plasma fraction with one volume of a solution containing 2.5 g of polyethylene glycol, 9.0 g of NaCl, 98.88 g of tris maleate, dissolved in 1 liter of distilled water.

Example 2

Heptest HDR

Preparation of Plasma Fraction Mixture

One volume of the clarified, buffered plasma fraction resultant from Example 1 is combined with one volume of 20% lactose buffer and 100 mM tris maleate at pH 7.5, resulting in a mixture termed for convenience of this example, mixture A. To mixture A is added bovine fibrinogen to achieve a final concentration of added fibrinogen of 3 mg/mL, resulting in a mixture termed for convenience of this example, mixture B. To mixture B, cephalin (prepared according to the method provided in Bell et al., Nature, 174:880 (1954)) is added in ratios that can range from about 6:0.5 (mixture B:cephalin) to about 6:1 (mixture B:cephalin) resulting in a mixture termed for convenience of this example, mixture C.

Preparation of the Factor $X_a$ Solution

The Factor $X_a$ is prepared according to the method of Yin et al. (Biol. Chem. 243:112 (1968)). Four aliquots of the Factor $X_a$ solution are prepared by diluting Factor $X_a$ with a buffer at ratios of: 1:5/1:10/1:20/1:30 (Factor $X_a$:buffer) where the buffer contains 20% lactose, 250 mM calcium chloride, 1% PEG 6000, 1% BSA, and 100 mM Tris maleate at pH 7.5. In alternative experiments, four aliquots of the Factor $X_a$ solution are prepared by diluting Factor $X_a$ with a buffer at ratios of: 1:5/1:10/1:20/1:30 (Factor $X_a$:buffer) where the buffer contains 5% lactose, 50 mM calcium chloride, 150 mM NaCl, 1% glycine, 0.1% PEG 6000, 3% BSA, and 100 mM Tris maleate at pH 7.5. The resultant four solutions are different dilutions of a solution termed the Factor $X_a$ solution.

Control Plasma

Two normal human plasma (NHP) samples are prepared; a first with no added heparin, and a second with 3 units of bovine or porcine heparin added per ml NHP.

Coagulation Assay

The four different dilutions of Factor $X_a$ solution are then tested with mixture C using the two Control Plasmas in coagulation assays. In performing the coagulation assays, 0.1 mL mixture C, 0.1 mL Factor $X_a$ solution, and 0.5 mL Control Plasma are mixed, and the time until clot formation is monitored.

The appropriate dilution of Factor $X_a$ solution aliquot that can be used as the basis for subsequent steps of freezing and lyophilization is the dilution that gives a clotting time of about 10-13 seconds for Control Plasma with no heparin, and a clotting time of about 35-50 seconds for Control Plasma with 3 units heparin/mL. When the dilution of the Factor $X_a$ solution with the clotting profile closest to the above is the most or least diluted of the aliquots, additional aliquots can be prepared, as needed, to determine an optimized dilution with the above coagulation time profile for the two Control Plasmas. When the dilution of the Factor $X_a$ solution with a clotting time within about 35-50 seconds for Control Plasma with 3 units heparin/mL, has a clotting time less than about 10 seconds for Control Plasma with 0 units heparin/mL, benzamidine HCl can be incrementally added to mixture C in ratios of about 60:1 (mixture C:200 mM benzamidine HCl), until the clotting time for Control Plasma with 0 units heparin/mL is about 10-13 seconds. Alternatively, when the dilution of the Factor $X_a$ solution with a clotting time within about 40-55 seconds for Control Plasma with 3 units heparin/mL, has a clotting time less than about 15 seconds for Control Plasma with 0 units heparin/mL, benzamidine HCl can be incrementally added to mixture C in ratios of about 60:1 (mixture C:200 mM benzamidine HCl), until the clotting time for Control Plasma with 0 units heparin/mL is about 15-20 seconds.

Upon determining the optimized dilution of Factor $X_a$ solution and the optimized amount of benzamidine HCl to add, mixture C is combined with benzamidine HCl according to the optimized ratio, and Factor $X_a$ is diluted with buffer according to the optimized Factor $X_a$ solution dilution. The resultant mixture C and Factor $X_a$ solutions can then be used to prepare the coagulation assay composition.

Example 3

Heptest POC

Preparation of Plasma Fraction Mixture

The clarified, buffered plasma fraction resultant from Example 1 is combined with cephalin, normal human plasma, prothrombin complex, heparin and buffer containing 20% lactose and 100 mM tris maleate at pH 7.5 in the following ratio: 30 mL of Example 1 plasma fraction: 40 mL cephalin: 50 mL heparinized normal human plasma (NHP with 1 unit/mL heparin): 2 mL prothrombin complex: 60 mL buffer: 50-300 units heparin. The amount of heparin to be used can be selected according to the desired clotting time. The components can be added in any order. The resultant mixture is termed for convenience of this example, mixture D.

Preparation of the Factor $X_a$ Solution

Factor $X_a$ solution and dilutions thereof are prepared as provided in Example 2.

Control Plasma

Two normal human plasma samples are prepared; a first with no added heparin, and a second with 7.5 units of heparin added per ml NHP.

Coagulation Assay

The different dilutions of Factor $X_a$ solution are then tested with mixture D using the two Control Plasmas in coagulation assays. In performing the coagulation assays, 0.1 mL mixture D, 0.1 mL Factor $X_a$ solution, and 0.5 mL Control Plasma are mixed, and the time until clot formation is monitored.

The appropriate dilution of Factor $X_2$ solution aliquot that can be used as the basis for subsequent steps of freezing and lyophilization is the dilution that gives a clotting time of about 13-17 seconds for Control Plasma with no heparin, and a clotting time of less than about 100 seconds for Control Plasma with 7.5 units heparin/mL. When the dilution of the Factor $X_a$ solution with the clotting profile closest to the above is the most or least diluted of the aliquots, additional aliquots can be prepared, as needed, to determine an optimized dilution with the above coagulation time profile for the two Control Plasmas. When the dilution of the Factor $X_a$ solution with a clotting time less than about 100 seconds for Control Plasma with 7.5 units heparin/mL, has a clotting time less than about 13 seconds for Control Plasma with 0 units heparin/mL, further dilutions of the Factor $X_a$ solution can be used, or mixture D can be prepared where the amount of cephalin is reduced relative to the remaining components. Modifications to the Factor $X_a$ solution and/or mixture D, and further clotting test can be performed iteratively until the clotting time for Control Plasma with 0 units heparin/mL is about 13-17 seconds and the clotting time for Control Plasma with 7.5 units heparin/mL is less than about 100 seconds.

Upon determining the optimized dilution of Factor $X_a$ solution, and the optimized amount of cephalin to add to mixture D, mixture D is combined according to the optimized cephalin ratio, and Factor $X_a$ is diluted with buffer according to the optimized Factor $X_a$ solution dilution. The resultant mixture D and Factor $X_a$ solutions can then be used to prepare the coagulation assay composition.

Example 4

A glass vial with a 2.4 mm steel ball is cooled to about −90° C. Into the −90° C. glass vial is placed 100 μl of the plasma fraction mixture resultant from Example 2 or Example 3, and the plasma fraction mixture freezes instantly. The vial is maintained at −90° C. Next, 100 μl of the Factor $X_a$ solution resultant from Example 2 or Example 3 is added to the −90° C. glass vial, and the Factor $X_a$ solution freezes instantly. The vial is then placed into a lyophilizer at standard settings for about 8 hours. The vial is then sealed under vacuum, and then removed from the lyophilizer. The vial can be stored at room temperature.

Example 5

The vial containing the coagulation assay composition of Example 2 or Example 3, as lyophilized and having a steel ball added in Example 4, can be used in coagulation assays. A fresh blood sample is added to a vial containing 3.8% sodium citrate, where the ratio of blood to sodium citrate is 9:1. A 0.5 mL aliquot of the blood/sodium citrate solution is dispensed into the vial containing the coagulation assay composition and steel ball, and a timer is started. The vial is placed on a vortex mixture for about 3-5 seconds to mix the blood and lyophilized coagulation assay composition. The vial is then placed in a Behnk Thrombostat Coagulometer that is configured to monitor the motion of the 2 mm steel ball. The steel ball is monitored until its motion is impaired by a solid clot formed in the vial. At the time of solid clot formation, the timer is stopped, and the time period from adding the blood mixture to the vial until solid clot formation is noted as the resulting clotting time of the assay.

Standard calibration curves can be prepared by adding known amounts of anticoagulant such as heparin or hirudin to blood or NHP, and performing the above coagulation assay to obtain a series of clotting times as a function of heparin concentration, as shown in FIG. 1.

What is claimed is:

1. A blood coagulation assay composition comprising components:
    a) partially or substantially pure Factor X or Factor Xa,
    b) Factor V or Factor Va,
    c) a multivalent cation,
    wherein the components of the composition are substantially unreacted with one another,
    wherein the composition is present in a single chamber vessel and
    wherein the composition is formed by, in either order,
    placing an aqueous solution comprising component a) the Factor X or
    Factor Xa and c) the multivalent cation in the vessel and
    freezing the solution,
    placing an aqueous solution comprising component b) the Factor V or
    Factor Va in the same vessel,
    freezing the solution, and
    lyophilizing the frozen solution until substantially all water is removed from the vessel, wherein the latter performed placing step is conducted substantially without allowing the previous solution to transition to liquid form.
2. The composition of claim 1, wherein the composition is substantially free of products of a clotting reaction.
3. The composition of claim 1, further characterized by providing a linear anticoagulant curve when anticoagulant concentration is plotted versus clotting time.
4. The composition of claim 1 wherein the multivalent cation is a calcium salt.
5. The composition of claim 4, wherein the calcium salt is calcium chloride.
6. The composition of claim 1, further comprising a phospholipid or detergent.
7. The composition of claim 6, wherein the phospholipid is cephalin.
8. The composition of claim 1, wherein component b) is a component of a plasma fraction.
9. The composition of claim 1, further comprising fibrinogen.
10. The composition of claim 1, wherein component b) is a plasma fraction containing Factor V or Factor Va and which further comprises fibrinogen and phospholipid or detergent.
11. The composition of claim 1, wherein component b) is a plasma fraction containing Factor V and which further comprises prothrombin complex, anticoagulant, phospholipid or detergent and normal plasma.
12. The composition of claim 1, wherein the composition provides a linear correlation between clotting time and heparin concentration range, wherein the heparin concentration range is selected from the group consisting of 0 units/ml to about 20 units/ml, 0 units per/ml to about 15 units/ml, 0 units per/ml to about 12 units/ml, 0 units per/ml to about 10 units/ml, 0 units per/ml to about 7.5 units/ml, and 0 units per/ml to about 5 units/ml.
13. The composition of claim 1, wherein component a) is Factor Xa.
14. The composition of claim 1, wherein component b) is Factor V.
15. The composition of claim 1, further comprising benzamidine.
16. The composition of claim 1, wherein the vessel is sealed with a vapor-impermeable seal.
17. The composition of claim 1, wherein a steel ball is located within the vessel.
18. A kit comprising the composition of claim 1, further including a reference for quantitating the results of a coagulation assay.
19. A method for preparing the blood coagulation assay composition of claim 1 comprising:
    placing a solution comprising partially or substantially pure Factor X or Factor Xa and a multivalent cation in a single chamber vessel,
    freezing the solution,
    placing a solution comprising Factor V or Factor Va in the same vessel,
    freezing the solution,
    lyophilizing the frozen solution until substantially all water is removed from the vessel, wherein the placing steps may be in either order and wherein the latter performed placing step is conducted substantially without allowing the previous solution to transition to liquid form.
20. A method of assaying coagulation of a sample comprising:
    a) mixing a sample with the coagulation assay composition of claim 1 and,
    b) determining the time period beginning upon performing step a) and ending upon clot formation.

* * * * *